(12) United States Patent
Korth et al.

(10) Patent No.: US 7,186,768 B2
(45) Date of Patent: Mar. 6, 2007

(54) SILANE-MODIFIED OXIDIC OR SILICEOUS FILLER, PROCESS FOR ITS PRODUCTION AND ITS USE

(75) Inventors: Karsten Korth, Wyhlen (DE); Kurt Eichenauer, Bad Sodensalmünster (DE); Reimund Pieter, Bensheim (DE); Oliver Klockmann, Köln (DE); Jürgen Heidlas, Trostberg (DE); Martin Ober, Altenmarkt (DE); Rudolf Zobel, Willanzheim (DE)

(73) Assignee: Degussa AG, Düsseldorf (DE)

( * ) Notice: Subject to any disclaimer, the term of this patent is extended or adjusted under 35 U.S.C. 154(b) by 612 days.

(21) Appl. No.: 10/423,901

(22) Filed: Apr. 25, 2003

(65) Prior Publication Data

US 2003/0200900 A1     Oct. 30, 2003

(30) Foreign Application Priority Data

Apr. 25, 2002  (DE) ............................... 102 18 350

(51) Int. Cl.
*C08K 3/18*     (2006.01)
(52) U.S. Cl. ..................... 524/430; 106/409
(58) Field of Classification Search ............. 524/430; 106/409
See application file for complete search history.

(56) References Cited

U.S. PATENT DOCUMENTS

| | | | |
|---|---|---|---|
| 3,227,675 A | 1/1966 | Papalos | |
| 3,567,680 A | 3/1971 | Iannicelli | |
| 3,978,103 A | 8/1976 | Meyer-Simon et al. | |
| 3,997,356 A | 12/1976 | Thurn et al. | |
| 4,044,037 A | 8/1977 | Mui et al. | |
| 4,076,550 A | 2/1978 | Thurn et al. | |
| 4,151,154 A | 4/1979 | Berger | |
| 6,013,234 A | 1/2000 | Ray et al. | |
| 6,022,404 A | 2/2000 | Ettlinger et al. | |
| 6,413,490 B1 | 7/2002 | Gilges et al. | |
| 2003/0082090 A1 | 5/2003 | Blume et al. | |

FOREIGN PATENT DOCUMENTS

| | | |
|---|---|---|
| DE | 2 141 159 | 3/1973 |
| DE | 2 212 239 | 10/1973 |
| DE | 24 05 758 | 8/1975 |
| DE | 25 42 534 | 3/1977 |
| DE | 30 14 007 | 10/1980 |
| DE | 33 14 742 | 10/1984 |
| DE | 195 41 404 | 5/1997 |
| DE | 197 34 295 C1 | 2/1999 |
| DE | 199 28 851 A1 | 12/2000 |
| DE | 101 22 269 | 11/2002 |
| EP | 0 126 871 | 12/1984 |
| EP | 1 295 850 A1 | 3/2003 |

OTHER PUBLICATIONS

European Search Report, dated Sep. 4, 2003, issued by the European Patent Office, for European Patent Application No. EP 03007875.2 (4 pages).

*Primary Examiner*—Samuel Barts
(74) *Attorney, Agent, or Firm*—Smith, Gambrell & Russell, LLP

(57) ABSTRACT

Silane-modified oxidic or siliceous filler with a bead fraction below 75 μm of less than 15 wt. % and a median particle size distribution between of 150 to 500 μm, which is produced by the reaction of at least one microbeaded or microgranular, oxidic or siliceous filler in a compressed gas with at least one silane. The silane-modified oxidic or siliceous fillers are used in rubber compounds.

37 Claims, No Drawings

SILANE-MODIFIED OXIDIC OR SILICEOUS FILLER, PROCESS FOR ITS PRODUCTION AND ITS USE

INTRODUCTION AND BACKGROUND

The present invention relates to a silane-modified oxidic or siliceous filler, a process for its production and its use.

The treatment of oxidic or siliceous compounds with organosilicon compounds in order by this treatment to strengthen the bond between the inorganic filler and the organic polymer used in filler-reinforced elastomers and thereby to improve the properties of the fillers in the polymers is known.

It is known from DE 2141159, DE 2212239 and U.S. Pat. No. 3,978,103 that sulfur-containing organosilicon compounds, such as bis-(3-triethoxysilyipropyl) tetrasulfide or 3-mercaptopropyl triethoxysilane, are used as the silane coupling agent or reinforcing filler in oxidic-filled rubber compounds, inter alia for tire treads and other parts of car tires.

In order to circumvent the considerable problems that arise during the processing of mercaptosilanes, such as pre-scorch, scorch and plasticity properties for example, it is known that mostly polysulfidic organosilanes, such as for example bis-(3-triethoxysilylpropyl) tetrasulfide or bis-(3-triethoxysilylpropyl) disulfide (DE 2542534, DE2405758, DE19541404, DE19734295), which for silica-filled vulcanizates represent a compromise in terms of vulcanizing safety, simple production and reinforcing performance, can be used as a coupling agent for tire components.

The known incorporation of the corresponding additives, especially organosilanes and the unmodified fillers, into the unvulcanized polymer blends can be performed in various ways.

The in-situ method involves a joint process for mixing fillers, such as carbon black and silica, with organosilanes and the polymers used.

The ex-situ method involves modifying the filler with the corresponding organosilane or a mixture of various organosilanes, before the filler is processed with the polymer to form the unvulcanized rubber mix.

Also known is the addition of organosilanes in liquid form (U.S. Pat. No. 3,997,356) during production of the unvulcanized mix for rubber compounds or the addition of the active filler via a physical mixture of organosilane and filler prepared in advance (DE 3314742, U.S. Pat. No. 4,076,550). The disadvantage of these mixtures, which have undergone no thermal pretreatment, is the poor storage stability and hence the often inadequate property stability of the products.

U.S. Pat. No. 4,151,154 describes oxidic siliceous fillers whose surface is treated with two different types of organosilicon compounds. The oxidic particles are treated in such a way that they display a greater affinity to water and can also be dispersed more easily in aqueous systems.

The modification of kaolin suspended in water with various organosilanes is known from U.S. Pat. No. 3,567,680. However, the organosilicon compounds that are described are water-soluble in the quantities required for modification, such that in this case the filler can be treated from an aqueous solution.

U.S. Pat. No. 4,044,037 describes aryl polysulfides and mineral fillers treated with these compounds, which are used in rubber compounds. They are produced in an aqueous/alcohol formulation containing 80 to 99.9 wt. % alcohol.

A process is also known from EP 01 26 871 wherein the surface of siliceous fillers is modified with the aid of an aqueous emulsion of water-insoluble organosilicon compounds.

It is known that the surface of fillers can be modified by dissolving the organosilicon compound in an organic solvent with subsequent treatment of the fillers, e.g. clays (U.S. Pat. No. 3,227,675).

The known processes for modifying fillers for rubber and plastic applications with surface-active organosilanes or mixtures thereof have the disadvantage of being based on the use of water, organic solvents or direct spraying of the organosilicon compound onto the surface of the filler with a subsequent heat treatment, the conditioning reaction. The known water-insoluble rubber-typical organosilanes can often be effectively chemically bonded with fillers only in hydrocarbon-based solvents, most of which are toxic and readily flammable.

The known fillers modified ex situ with organosilanes have the disadvantage that until now the rubber properties have tended to be not better but in fact poorer than is the case with fillers and silanes mixed together in situ.

In addition, in the case of fillers having a large specific surface area or a pronounced surface texture, silanization is often not homogeneous. Diffusion of the silane molecules into underlying layers of highly porous fillers, such as precipitated silicas for example, can be achieved only incompletely if at all with the modification methods known until now. Macroscopically preformed fillers are therefore modified only inadequately and incompletely by the known silanization processes.

In addition, preformed fillers cannot be silanized successfully and non-destructively or with low abrasion by means of the known silanization processes and the subsequent drying process that is often necessary. The structure of preformed fillers is or would be destroyed or damaged with the known processes (U.S. Pat. No. 4,151,154; DE 3314742 C2; U.S. Pat. No. 3,567,680). Thus, for example, silica granules formed on rolls (DE 3014007) are very rapidly broken down into a poorer quality silica powder (higher dust and fines content) by being introduced into a mixer or similar equipment and kept in motion for an extended period of time.

A process for reacting at least one biopolymeric, biooligomeric, oxidic or siliceous filler in a compressed gas with at least one silane is known from DE 10122269.6.

The use of powdered and granular fillers therein described is disadvantageous. Powdered silicas are disadvantageous in industrial conditions, for example because of their high dust content, low bulk density, poor flow properties and hence commonly poor meterability. Granules can subsequently be obtained from powdered silicas by mechanical compaction. Since this means an additional processing step, manufacturers try to avoid such processes due to economic considerations. These granules easily break down again into the powdered starting material under mechanical loading and in addition the applicational properties of the silicas frequently deteriorate due to the subsequent granulation and associated mechanical loading of the particles.

An object of the present invention is to produce a low-dust silane-modified oxidic or siliceous filler directly from a low-dust microbeaded or microgranular, oxidic or siliceous filler. The silane-modified oxidic or siliceous filler should display a satisfactory, quantitatively easily variable coverage with the corresponding rubber-reactive silanes and, in addition, comparable or better properties than known silane-filler mixtures produced in situ and, in addition, better rubber properties in the rubber than known silane-filler mixtures produced ex situ.

A further object of the invention is to be able to work or process the microbeaded or microgranular, oxidic or siliceous filler to be modified in a low-dust supply form. The external, macroscopic shape of these preformed microbeaded or microgranular, oxidic or siliceous fillers should be largely maintained during the modification process. A largely dust-free or low-dust silane-modified oxidic or siliceous filler should be obtained.

A still further object of the present invention is to provide a process for modifying microbeaded or microgranular, oxidic or siliceous fillers with silanes, wherein the modification reaction is not performed in water or organic solvents.

Yet another object of the present invention is to provide a variety of products containing the low dust silane modified oxidic or siliceous filler described herein.

SUMMARY OF THE INVENTION

The above and other objects of the present invention can be achieved by a silane-modified oxidic or siliceous filler, which is characterized in that the bead fraction below 75 µm (fines or dust content) is less than 15 wt. %, preferably less than 10 wt. %, particularly preferably less than 7 wt. %, especially preferably less than 5 wt. %, determined by screen analysis, and that the median particle size is between 130 µm and 500 µm, preferably between 130 µm and 450 µm, particularly preferably between 150 µm and 400 µm, especially preferably between 175 µm and 350 µm, determined by laser diffraction without ultrasonic treatment.

The filler according to the invention can display a statistically determined mean shape factor greater than 0.805, preferably greater than 0.82, particularly preferably greater than 0.84, especially preferably greater than 0.86.

The filler according to the invention can display a statistically determined mean circle factor greater than 0.55, preferably greater than 0.57, particularly preferably greater than 0.60, and especially preferably greater than 0.62.

The filler according to the invention can display micropores in the <2 nm range of between 0 and 0.5 ml/g, preferably between 0 and 0.3 ml/g, particularly preferably between 0 and 0.1 ml/g.

The filler according to the invention can display mesopores in the range between 2 and 30 nm of between 0 and 1 ml/g, preferably between 0 and 0.75 ml/g, particularly preferably between 0 and 0.5 ml/g.

The filler according to the invention can display mesopores in the range between 2 and 50 nm of between 0 and 5 ml/g, preferably between 0 and 2.5 ml/g, particularly preferably between 0 and 1.5 ml/g.

The filler according to the invention can display macropores in the range above 30 nm of between 0 and 10 ml/g, preferably between 0 and 7.5 ml/g, particularly preferably between 0 and 5 ml/g.

The filler according to the invention can display macropores in the range above 50 nm of between 0 and 10 ml/g, preferably between 0 and 7.5 ml/g, particularly preferably between 0 and 5 ml/g.

The filler according to the invention can display a BET surface area of between 0.5 $m^2/g$ and 500 $m^2/g$, preferably between 0.5 and 300 $m^2/g$, particularly preferably between 0.5 and 250 $m^2/g$.

The filler according to the invention can display Sears numbers (consumption of 0.1 KOH) of between 1 and 50 ml per 5 g sample.

The filler according to the invention can display a sulfur content in pure or chemically bonded form of between 0.05 and 25 wt. %, preferably between 0.05 and 10 wt. %, particularly preferably between 0.05 and 4 wt. %.

The filler according to the invention can display a carbon content in pure or chemically bonded form of between 0.1 and 25 wt. %, preferably between 0.1 and 10 wt. %, particularly preferably between 0.1 and 5 wt. %.

The filler according to the invention can display a content of physically and chemically bonded alcohol of between 0 and 25 wt. %, preferably between 0 and 15 wt. %, particularly preferably between 0 and 10 wt. %.

The filler according to the invention can display a chemically or physically bonded residual content of the alcohol deriving from the silane of less than 75 mol %, preferably less than 50 mol %, particularly preferably less than 30 mol %, especially preferably less than 20 mol %, of the initial amount of alcohol in the silane used.

The silane-modified oxidic or siliceous filler according to the invention can be predominantly bead-shaped, spherical, round and/or homogeneously shaped.

The silane-modified oxidic or siliceous filler according to the invention can be obtainable by reacting at least one microbeaded or microgranular, oxidic or siliceous filler in a compressed gas with at least one silane.

The silane-modified oxidic or siliceous filler according to the invention can contain 0.1 to 50 wt. %, preferably 0.1 to 25.0 wt. %, particularly preferably 0.1 to 10 wt. % silane.

The silane-modified oxidic or siliceous filler according to the invention can contain 50 to 99.9 wt. % microbeaded or microgranular, oxidic or siliceous filler.

The bead distribution in the silane-modified oxidic or siliceous filler according to the invention, which can be determined by screening, can be the same as or similar to the bead distribution in the untreated microbeaded or microgranular, oxidic or siliceous filler determined by screening.

The percentage difference in the bead fractions, determined by screen analysis, between the starting material, a microbeaded or microgranular, oxidic or siliceous filler, and the end product, a silane-modified oxidic or siliceous filler, for the bead fraction below 75 µm and the bead fraction between 75 and 150 µm, can be not more than 100 wt. %, preferably not more than 75 wt. %, particularly preferably not more than 50 wt. %, especially preferably not more than 20 wt. %.

The ratio of the two screen fractions >300 µm and 150 µm–300 µm can be less than 10:1, preferably less than 7:1, particularly preferably less than 4:1.

The silane-modified oxidic or siliceous filler according to the invention can display a bead fraction above 1000 µm of less than 30 wt. %, preferably less than 20 wt. %, particularly preferably less than 10 wt. %.

The silane-modified oxidic or siliceous filler according to the invention can display a bead fraction above 500 µm of less than 30 wt. %, preferably less than 20 wt. %, particularly preferably less than 10 wt. %.

The silane can be chemically and/or physically bonded to the surface of the fillers.

The invention also provides a process for the production of a silane-modified oxidic or siliceous filler, which is characterized in that at least one microbeaded or microgranular, oxidic or siliceous filler is reacted with at least one silane in a gas compressed by means of pressure and/or temperature.

DETAILED DESCRIPTION OF THE INVENTION

An organosilicon compound or mixtures of organosilicon compounds having the general formula (I)

$$Z-A-S_x-A-Z \quad (I)$$

can be used as the silane, in which formula
x is a number from 1 to 14, preferably 1 to 8, particularly preferably 2 to 6,
Z equals $SiX^1X^2X^3$ and
$X^1$, $X^2$, $X^3$ can each mutually independently denote hydrogen (—H),
halogen (—Cl, —Br, —I) or hydroxy (—OH),
an alkyl substituent, preferably methyl, ethyl, propyl or butyl,
an alkyl acid substituent $(C_xH_{2x+1})$—C(=O)O—, alkenyl acid
substituent, for example acetoxy $CH_3$—(C=O)O—,
a substituted alkyl or alkenyl acid substituent, for example oximato-$R^1{}_2C$=NO—,
a linear or branched, cyclic hydrocarbon chain with 1–8 carbon atoms,
a cycloalkane radical with 5–12 carbon atoms,
a benzyl radical or a halogen- or alkyl-substituted phenyl radical, alkoxy groups, preferably ($C_1$–$C_{24}$) alkoxy, particularly preferably methoxy ($CH_3O$—) or ethoxy ($C_2H_5O$—), and dodecyloxy ($C_{12}H_{25}O$—), tetradecyloxy ($C_{14}H_{29}O$—), hexadecyloxy $C_{16}H_{33}O$—) and octadecyloxy-($C_{18}H_{37}O$—), with linear or branched hydrocarbon chains having ($C_{1-24}$) atoms, alkoxy groups with linear or branched polyether chains having $C_1$–$C_{24}$ atoms,
a cycloalkoxy group having ($C_{5-12}$) atoms,
a halogen- or alkyl-substituted phenoxy group or
a benzyloxy group,
A is a linear or branched, saturated or unsaturated aliphatic, aromatic or mixed aliphatic/aromatic divalent hydrocarbon chain comprising $C_1$–$C_{30}$, preferably $C_1$–$C_3$, particularly preferably (—$CH_2$—), (—$CH_2$—)$_2$, (—$CH_2$—)$_3$, (—$CH(CH_3)$—$CH_2$—) or (—$CH_2$—$CH(CH_3)$—).

A can be linear or branched and can contain saturated as well as unsaturated bonds. Rather than hydrogen substituents, A can be provided with a wide range of substituents, such as e.g. —CN, halogens, for example —Cl, —Br or —F, alcohol functionalities —OH, alkoxides —$OR^1$ or —O—(C=O)—$R^1$ ($R^1$=alkyl, aryl). $CH_2$, $CH_2CH_2$, $CH_2CH_2CH_2$, $CH_2CH(CH_3)$, $CH_2CH_2CH_2CH_2$, $CH_2CH_2CH(CH_3)$, $CH_2CH(CH_3)CH_2$, $CH_2CH_2CH_2CH_2CH_2$, $CH_2CH(CH_3)CH_2CH_2$, $CH_2CH_2CH(CH_3)CH_2$, $CH(CH_3)CH_2CH_2CH_2$ or $CH_2CH(CH_3)CH(CH_3)$ can preferably be used as A.

The following compounds can be used for example as the silane having the general formula (1):

[(MeO)$_3$Si(CH$_2$)$_3$]$_2$S, [(MeO)$_3$Si(CH$_2$)$_3$]$_2$S$_2$, [(MeO)$_3$Si(CH$_2$)$_3$]$_2$S$_3$,
[(MeO)$_3$Si(CH$_2$)$_3$]$_2$S$_4$, [(MeO)$_3$Si(CH$_2$)$_3$]$_2$S$_5$, [(MeO)$_3$Si(CH$_2$)$_3$]$_2$S$_6$,
[(MeO)$_3$Si(CH$_2$)$_3$]$_2$S$_7$, [(MeO)$_3$Si(CH$_2$)$_3$]$_2$S$_8$, [(MeO)$_3$Si(CH$_2$)$_3$]$_2$S$_9$,
[(MeO)$_3$Si(CH$_2$)$_3$]$_2$S$_{10}$, [(MeO)$_3$Si(CH$_2$)$_3$]$_2$S$_{11}$,
[(MeO)$_3$Si(CH$_2$)$_3$]$_2$S$_9$, [(EtO)$_3$Si(CH$_2$)$_3$]$_2$S, [(EtO)$_3$Si(CH$_2$)$_3$]$_2$S$_2$,
[(EtO)$_3$Si(CH$_2$)$_3$]$_2$S$_3$, [(EtO)$_3$Si(CH$_2$)$_3$]$_2$S$_4$, [(EtO)$_3$Si(CH$_2$)$_3$]$_2$S$_5$,
[(EtO)$_3$Si(CH$_2$)$_3$]$_2$S$_6$, [(EtO)$_3$Si(CH$_2$)$_3$]$_2$S$_7$, [(EtO)$_3$Si(CH$_2$)$_3$]$_2$S$_8$,
[(EtO)$_3$Si(CH$_2$)$_3$]$_2$S$_9$, [(EtO)$_3$Si(CH$_2$)$_3$]$_2$S$_{10}$, [(EtO)$_3$Si(CH$_2$)$_3$]$_2$S$_{11}$,
[(EtO)$_3$Si(CH$_2$)$_3$]$_2$S$_{12}$, [(EtO)$_3$Si(CH$_2$)$_3$]$_2$S$_{13}$,
[(EtO)$_3$Si(CH$_2$)$_3$]$_2$S$_{14}$, [(C$_3$H$_7$O)$_3$Si(CH$_2$)$_3$]$_2$S,
[(C$_3$H$_7$O)$_3$Si(CH$_2$)$_3$]$_2$S$_2$, [(C$_3$H$_7$O)$_3$Si(CH$_2$)$_3$]$_2$S$_3$,
[(C$_3$H$_7$O)$_3$Si(CH$_2$)$_3$]$_2$S$_4$, [(C$_3$H$_7$O)$_3$Si(CH$_2$)$_3$]$_2$S$_5$,
[(C$_3$H$_7$O)$_3$Si(CH$_2$)$_3$]$_2$S$_6$, [(C$_3$H$_7$O)$_3$Si(CH$_2$)$_3$]$_2$S$_7$,
[(C$_3$H$_7$O)$_3$Si(CH$_2$)$_3$]$_2$S$_8$, [(C$_3$H$_7$O)$_3$Si(CH$_2$)$_3$]$_2$S$_9$,
[(C$_3$H$_7$O)$_3$Si(CH$_2$)$_3$]$_2$S$_{10}$, [(C$_3$H$_7$O)$_3$Si(CH$_2$)$_3$]$_2$S$_{11}$,
[(C$_3$H$_7$O)$_3$Si(CH$_2$)$_3$]$_2$S$_{12}$, [(C$_3$H$_7$O)$_3$Si(CH$_2$)$_3$]$_2$S$_{13}$ or [(C$_3$H$_7$O)$_3$Si(CH$_2$)$_3$]$_2$S$_{14}$ or (C$_{12}$H$_{25}$O)(EtO)$_2$Si(CH$_2$)$_3$]S$_x$[(CH$_2$)$_3$Si(OEt)$_3$],
[(C$_{12}$H$_{25}$O)$_2$(EtO)Si(CH$_2$)$_3$]S$_x$[(CH$_2$)$_3$Si(OEt)$_3$],
[(C$_{12}$H$_{25}$O)$_3$Si(CH$_2$)$_3$]S$_x$[(CH$_2$)$_3$Si(OEt)$_3$],
[(C$_{12}$H$_{25}$O)(EtO)$_2$Si(CH$_2$)$_3$]S$_x$[(CH$_2$)$_3$Si(C$_{12}$H$_{25}$O)(OEt)$_2$],
[(C$_{12}$H$_{25}$O)$_2$(EtO)Si(CH$_2$)$_3$]S$_x$[(CH$_2$)$_3$Si(C$_{12}$H$_{25}$O)(OEt)$_2$],
[(C$_{12}$H$_{25}$O)$_3$Si(CH$_2$)$_3$]S$_x$[(CH$_2$)$_3$Si(C$_{12}$H$_{25}$O)(OEt)$_2$],
[(C$_{12}$H$_{25}$O)(EtO)$_2$Si(CH$_2$)$_3$]S$_x$[(CH$_2$)$_3$Si(C$_{12}$H$_{25}$O)$_2$(OEt)],
[(C$_{12}$H$_{25}$O)$_2$(EtO)Si(CH$_2$)$_3$]S$_x$[(CH$_2$)$_3$Si(C$_{12}$H$_{25}$O)$_2$(OEt)],
[(C$_{12}$H$_{25}$O)$_3$Si(CH$_2$)$_3$]S$_x$[(CH$_2$)$_3$Si(C$_{12}$H$_{25}$O)$_2$(OEt)],
[(C$_{12}$H$_{25}$O)(EtO)$_2$Si(CH$_2$)$_3$]S$_x$[(CH$_2$)$_3$Si(C$_{12}$H$_{25}$O)$_3$],
[(C$_{12}$H$_{25}$O)$_2$(EtO)Si(CH$_2$)$_3$]S$_x$[(CH$_2$)$_3$Si(C$_{12}$H$_{25}$O)$_3$],
[(C$_{12}$H$_{25}$O)$_3$Si(CH$_2$)$_3$]S$_x$[(CH$_2$)$_3$Si(C$_{12}$H$_{25}$O)$_3$],
(C$_{14}$H$_{29}$O)(EtO)$_2$Si(CH$_2$)$_3$]S$_x$[(CH$_2$)$_3$Si(OEt)$_3$],
[(C$_{14}$H$_{29}$O)$_2$(EtO)Si(CH$_2$)$_3$]S$_x$[(CH$_2$)$_3$Si(OEt)$_3$],
[(C$_{14}$H$_{29}$O)$_3$Si(CH$_2$)$_3$]S$_x$[(CH$_2$)$_3$Si(OEt)$_3$],
[(C$_{14}$H$_{29}$O)(EtO)$_2$Si(CH$_2$)$_3$]S$_x$[(CH$_2$)$_3$Si(C$_{14}$H$_{29}$O)(OEt)$_2$],
[(C$_{14}$H$_{29}$O)$_2$(EtO)Si(CH$_2$)$_3$]S$_x$[(CH$_2$)$_3$Si(C$_{14}$H$_{29}$O)(OEt)$_2$],
[(C$_{14}$H$_{29}$O)$_3$Si(CH$_2$)$_3$]S$_x$[(CH$_2$)$_3$Si(C$_{14}$H$_{29}$O)(OEt)$_2$],
[(C$_{14}$H$_{29}$O)(EtO)$_2$Si(CH$_2$)$_3$]S$_x$[(CH$_2$)$_3$Si(C$_{14}$H$_{29}$O)$_2$(OEt)],
[(C$_{14}$H$_{29}$O)$_2$(EtO)Si(CH$_2$)$_3$]S$_x$[(CH$_2$)$_3$Si(C$_{14}$H$_{29}$O)$_2$(OEt)],
[(C$_{14}$H$_{29}$O)$_3$Si(CH$_2$)$_3$]S$_x$[(CH$_2$)$_3$Si(C$_{14}$H$_{29}$O)$_2$(OEt)],
[(C$_{14}$H$_{29}$O)(EtO)$_2$Si(CH$_2$)$_3$]S$_x$[(CH$_2$)$_3$Si(C$_{14}$H$_{29}$O)$_3$],
[(C$_{14}$H$_{29}$O)$_2$(EtO)Si(CH$_2$)$_3$]S$_x$[(CH$_2$)$_3$Si(C$_{14}$H$_{29}$O)$_3$],
[(C$_{14}$H$_{29}$O)$_3$Si(CH$_2$)$_3$]S$_x$[(CH$_2$)$_3$Si(C$_{14}$H$_{29}$O)$_3$],
(C$_{16}$H$_{33}$O)(EtO)$_2$Si(CH$_2$)$_3$]S$_x$[(CH$_2$)$_3$Si(OEt)$_3$],
[(C$_{16}$H$_{33}$O)$_2$(EtO)Si(CH$_2$)$_3$]S$_x$[(CH$_2$)$_3$Si(OEt)$_3$],
[(C$_{16}$H$_{33}$O)$_3$Si(CH$_2$)$_3$]S$_x$[(CH$_2$)$_3$Si(OEt)$_3$],
[(C$_{16}$H$_{33}$O)(EtO)$_2$Si(CH$_2$)$_3$]S$_x$[(CH$_2$)$_3$Si(C$_{16}$H$_{33}$O)(OEt)$_2$],
[(C$_{16}$H$_{33}$O)$_2$(EtO)Si(CH$_2$)$_3$]S$_x$[(CH$_2$)$_3$Si(C$_{16}$H$_{33}$O)(OEt)$_2$],
[(C$_{16}$H$_{33}$O)$_3$Si(CH$_2$)$_3$]S$_x$[(CH$_2$)$_3$Si(C$_{16}$H$_{33}$O)(OEt)$_2$],
[(C$_{16}$H$_{33}$O)(EtO)$_2$Si(CH$_2$)$_3$]S$_x$[(CH$_2$)$_3$Si(C$_{16}$H$_{33}$O)$_2$(OEt)],
[(C$_{16}$H$_{33}$O)$_2$(EtO)Si(CH$_2$)$_3$]S$_x$[(CH$_2$)$_3$Si(C$_{16}$H$_{33}$O)$_2$(OEt)],
[(C$_{16}$H$_{33}$O)$_3$Si(CH$_2$)$_3$]S$_x$[(CH$_2$)$_3$Si(C$_{16}$H$_{33}$O)$_2$(OEt)],
[(C$_{16}$H$_{33}$O)(EtO)$_2$Si(CH$_2$)$_3$]S$_x$[(CH$_2$)$_3$Si(C$_{16}$H$_{33}$O)$_3$],
[(C$_{16}$H$_{33}$O)$_2$(EtO)Si(CH$_2$)$_3$]S$_x$[(CH$_2$)$_3$Si(C$_{16}$H$_{33}$O)$_3$],
[(C$_{16}$H$_{33}$O)$_3$Si(CH$_2$)$_3$]S$_x$[(CH$_2$)$_3$Si(C$_{16}$H$_{33}$O)$_3$],
(C$_{18}$H$_{37}$O)(EtO)$_2$Si(CH$_2$)$_3$]S$_x$[(CH$_2$)$_3$Si(OEt)$_3$],
[(C$_{18}$H$_{37}$O)$_2$(EtO)Si(CH$_2$)$_3$]S$_x$[(CH$_2$)$_3$Si(OEt)$_3$],
[(C$_{18}$H$_{37}$O)$_3$Si(CH$_2$)$_3$]S$_x$[(CH$_2$)$_3$Si(OEt)$_3$],
[(C$_{18}$H$_{37}$O)(EtO)$_2$Si(CH$_2$)$_3$]S$_x$[(CH$_2$)$_3$Si(C$_{18}$H$_{37}$O)(OEt)$_2$],
[(C$_{18}$H$_{37}$O)$_2$(EtO)Si(CH$_2$)$_3$]S$_x$[(CH$_2$)$_3$Si(C$_{18}$H$_{37}$O)(OEt)$_2$],
[(C$_{18}$H$_{37}$O)$_3$Si(CH$_2$)$_3$]S$_x$[(CH$_2$)$_3$Si(C$_{18}$H$_{37}$O)(OEt)$_2$],
[(C$_{18}$H$_{37}$O)(EtO)$_2$Si(CH$_2$)$_3$]S$_x$[(CH$_2$)$_3$Si(C$_{18}$H$_{37}$O)$_2$(OEt)],
[(C$_{18}$H$_{37}$O)$_2$(EtO)Si(CH$_2$)$_3$]S$_x$[(CH$_2$)$_3$Si(C$_{18}$H$_{37}$O)$_2$(OEt)],
[(C$_{18}$H$_{37}$O)$_3$Si(CH$_2$)$_3$]S$_x$[(CH$_2$)$_3$Si(C$_{18}$H$_{37}$O)$_2$(OEt)],
[(C$_{18}$H$_{37}$O)(EtO)$_2$Si(CH$_2$)$_3$]S$_x$[(CH$_2$)$_3$Si(C$_{18}$H$_{37}$O)$_3$],
[(C$_{18}$H$_{37}$O)$_2$(EtO)Si(CH$_2$)$_3$]S$_x$[(CH$_2$)$_3$Si(C$_{18}$H$_{37}$O)$_3$],
[(C$_{18}$H$_{37}$O)$_3$Si(CH$_2$)$_3$]S$_x$[(CH$_2$)$_3$Si(C$_{18}$H$_{37}$O)$_3$], or generally
[(C$_y$H$_{2y+1}$O)(R)$_2$Si(CH$_2$)$_3$]S$_x$[(CH$_2$)$_3$Si(R)$_3$],
[(C$_y$H$_{2y+1}$O)$_2$(R)Si(CH$_2$)$_3$]S$_x$[(CH$_2$)$_3$Si(R)$_3$],
[(C$_y$H$_{2y+1}$O)$_3$Si(CH$_2$)$_3$]S$_x$[(CH$_2$)$_3$Si(R)$_3$],
[(C$_y$H$_{2y+1}$O)(R)$_2$Si(CH$_2$)$_3$]S$_x$[(CH$_2$)$_3$Si(C$_y$H$_{2y+1}$O)(R)$_2$],
[(C$_y$H$_{2y+1}$O)$_2$(R)Si(CH$_2$)$_3$]S$_x$[(CH$_2$)$_3$Si(C$_y$H$_{2y+1}$O)(R)$_2$],
[(C$_y$H$_{2y+1}$O)$_3$Si(CH$_2$)$_3$]S$_x$[(CH$_2$)$_3$Si(C$_y$H$_{2y+1}$O)(R)$_2$], $[(C_yH_{2y+1}O)(R)_2Si(CH_2)_3]S_x[(CH_2)_3Si(C_yH_{2y+1}O)_2(R)]$,
$[(C_yH_{2y+1}O)_2(R)Si(CH_2)_3]S_x[(CH_2)_3Si(C_yH_{2y+1}O)_2(R)]$,
$[(C_yH_{2y+1}O)_3Si(CH_2)_3]S_x[(CH_2)_3Si(C_yH_{2y+1}O)_2(R)]$,
$[(C_yH_{2y+1}O)(R)_2Si(CH_2)_3]S_x[(CH_2)_3Si(C_yH_{2y+1}O)_3]$,
$[(C_yH_{2y+1}O)_2(R)Si(CH_2)_3]S_x[(CH_2)_3Si(C_yH_{2y+1}O)_3]$ or
$[(C_yH_{2y+1}O)_3Si(CH_2)_3]S_x[(CH_2)_3Si(C_yH_{2y+1}O)_3]$, where x=1–14, y=10–24 and R=(MeO) or/and (EtO), or mixtures of the individual silanes cited above.

Compounds such as are described in DE 198 44 607 can also be used as the silane. DE 198 94 607 is relied on and incorporated herein by reference for the disclosure of the silanes.

An organosilicon compound or mixtures of organosilicon compounds having the general formula (II)

$$X^1X^2X^3Si\text{-}A\text{-}S\text{—}SiR^1R^2R^3 \quad (II)$$

can be used as the silane, in which formula $X^1$, $X^2$, $X^3$ and A mutually independently have the same meaning as in formula (I), $R^1$, $R^2$, $R^3$ are each mutually independent from one another and denote ($C_1$–$C_{16}$) alkyl, preferably ($C_1$–$C_4$) alkyl, particularly preferably methyl and ethyl, ($C_1$–$C_{16}$) alkoxy, preferably ($C_1$–$C_4$) alkoxy, particularly preferably methoxy and ethoxy, ($C_1$–$C_{16}$)haloalkyl, aryl, ($C_7$–$C_{16}$)aralkyl, —H, halogen or $X^1X^2X^3Si\text{-}A\text{-}S\text{—}$.

The following compounds can be used for example as the silane having the general formula (II):
$(EtO)_3$—Si—$(CH_2)_3$—S—Si$(CH_3)_3$, $[(EtO)_3$—Si—$(CH_2)_3$—S$]_2$Si$(CH_3)_2$,
$[(EtO)_3$—Si—$(CH_2)_3$—S$]_3$Si$(CH_3)$, $[(EtO)_3$—Si—$(CH_2)_3$—S$]_2$Si$(OEt)_2$,
$[(EtO)_3$—Si—$(CH_2)_3$—S$]_4$Si, $(EtO)_3$—Si—$(CH_2)_3$—S—Si$(OEt)_3$,
$(MeO)_3$—Si—$(CH_2)_3$—S—Si$(C_2H_5)_3$, $[(MeO)_3$—Si—$(CH_2)_3$—S$]_2$Si$(C_2H_5)_2$,
$[(MeO)_3$—Si—$(CH_2)_3$—S$]_3$Si$(CH_3)$, $[MeO)_3$—Si—$(CH_2)_3$—S$]_2$Si$(OMe)_2$,
$[(MeO)_3$—Si—$(CH_2)_3$—S$]_4$Si, $(MeO)_3$—Si—$(CH_2)_3$—S—Si$(OMe)_3$,
$EtO)_3$—Si—$(CH_2)_2$—CH$(CH_3)$—S—Si$(CH_3)_3$,
$(EtO)_3$—Si—$(CH_2)_2$—CH$(CH_3)$—S—Si$(C_2H_5)_3$,
$(EtO)_3$—Si—$(CH_2)_2$—CH$(CH_3)$—S—Si$(C_6H_5)_3$ or
$(EtO)_3$—Si—$(CH_2)_2(p\text{-}C_6H_4)$—S—Si$(CH_3)_3$.

An organosilicon compound or mixtures of organosilicon compounds having the general formula (III)

$$X^1X^2X^3Si\text{-}Alk \quad (III)$$

can be used as the silane, in which formula $X^1$, $X^2$ and $X^3$ each mutually independently have the same meaning as in formula (I) and Alk is a straight-chain, branched or cyclic ($C_1$–$C_{18}$) alkyl, for example methyl, ethyl, n-propyl, n-butyl, n-pentyl, n-hexyl, isopropyl or tert.-butyl, ($C_1$–$C_5$) alkoxy, for example methoxy, ethoxy, propoxy, butoxy, isopropoxy, isobutoxy, t-butoxy or pentoxy, halogen, for example fluorine, chlorine, bromine or iodine, hydroxy, thiol, nitrile, ($C_1$–$C_4$) haloalkyl, —NO$_2$, ($C_1$–$C_8$) thioalkyl, —NH$_2$, —NHR$^1$, —NR$^1$R$^2$, NH(SiX$^1$X$^2$X$^3$), alkenyl, allyl, vinyl, aryl or ($C_7$–$C_{16}$) aralkyl.

The term "alkenyl" as used herein is intended to include the vinyl group as well as straight-chain, branched or cyclic fragments, which can contain one or more carbon double bonds.

The term "cyclic alkyl or alkenyl fragments" as used herein is intended to include both monocyclic and bicyclic or polycyclic structures, as well as cyclic structures provided with alkyl substituents, for example norbornyl, norbornenyl, ethyl norbornyl, ethyl norbornenyl, ethyl cyclohexyl, ethyl cyclohexenyl or cyclohexyl cyclohexyl groups.

Aryl can be understood to include phenyls, biphenyls or other benzenoid compounds, which are optionally substituted with ($C_1$–$C_3$) alkyl, ($C_1$–$C_3$) alkoxy, halogen, hydroxy or with heteroatoms, such as NR$^1$R$^2$OR$^1$, PR$^1$R$^2$R$^3$, SH or SR$^1$.

The following compounds can be used for example as the silane having the general formula (III):
$(C_{12}H_{25}O)_3$—Si—$(CH_2)_{16}$—H, $(C_{14}H_{29}O)_3$—Si—$(CH_2)_{16}$—H,
$(C_{16}H_{33}O)_3$—Si—$(CH_2)_{16}$—H, $(C_{18}H_{37}O)_3$—Si—$(CH_2)_{16}$—H,
$(EtO)_3$—Si—$(CH_2)_3$—H, $(MeO)_3$—Si—$(CH_2)_3$—H, $(EtO)_3$—Si—C$(CH_3)_3$,
$(MeO)_3$—Si—C$(CH_3)_3$, $(EtO)_3$—Si—$(CH_2)_8$—H, $(MeO)_3$—Si—$(CH_2)_8$—H,
$(EtO)_3$—Si—$(CH_2)_{16}$—H, $(MeO)_3$—Si—$(CH_2)_{16}$—H, $(Me)_3$Si—(OMe),
$((Et)_3Si$—(OMe), $(C_3H_7)_3Si$—(OMe), $(C_6H_5)_3Si$—(OMe),
$(Me)_3Si$—(OEt), $((Et)_3Si$—(OEt), $(C_3H_7)_3Si$—(OEt),
$(C_6H_5)_3Si$—(OEt), $(Me)_3Si$—(OC$_3H_7$), $(Et)_3Si$—(OC$_3H_7$),
$(C_3H_7)_3Si$—(OC$_3H_7$), $(C_6H_5)_3Si$—(OC$_3H_7$), $(Me)_3SiCl$,
$(Et)_3SiCl$,
$(C_3H_7)_3SiCl$, $(C_6H_5)_3SiCl$, $Cl_3$—Si—CH$_2$—CH=CH$_2$,
$(MeO)_3$—Si—CH$_2$—CH=CH$_2$,
$(EtO)_3$—Si—CH$_2$—CH=CH$_2$, $(EtO)_3$—Si—CH$_2$—CH=CH$_2$ $Cl_3$—Si—CH=CH$_2$,
$(MeO)_3$—Si—CH=CH$_2$, $(EtO)_3$—Si—CH=CH$_2$,
$(Me_3Si)_2$ N—C(O)—H or $(Me_3Si)_2N$—H.

An organosilicon compound or a mixture of organosilicon compounds having the general formulae (IV) or (V)

$$[[(ROC(=O))_P\text{-}(G)]_k\text{—}Y\text{—}S]_r\text{-}G(SiX^1X^2X^3)_s \quad (IV)$$

$$[(X^1X^2X^3Si)_q\text{-}G]_a\text{—}[Y\text{—}[S\text{-}G\text{-}SiX^1X^2X^3]_b]_c \quad (V)$$

can be used as the silane, in which formulae Y represents a polyvalent species $(Q)_zD(=E)$, whereby the following applies: p is 0 to 5, r is 1 to 3, z is 0 to 2, q is 0 to 6, a is 0 to 7, b is 1 to 3, j is 0 to 1, but if p=1 it can also commonly be 0, c is 1 to 6, preferably 1 to 4, t is 0 to 5, s is 1 to 3, k is 1 to 2, under the proviso that (1) if (D) is a carbon, sulfur or sulfonyl, a+b=2 and k=1, (2) if (D) is a phosphorus atom, a+b=3 provided that c≧1 and b=1, whereby a=c+1, (3) if (D) is a phosphorus atom, k=2, Y represents a polyvalent species $(Q)_zD(=E)$, preferably
—C(=NR)—, —SC(=NR)—, —SC(=O)—, (—NR)C(=O)—, (—NR)C(=S)—,
—OC(=O)—, —OC(=S)—, —C(=O)—, —SC(=S)—, —C(=S)—, —S(=O)—,
—S(=O)$_2$—, —OS(=O)$_2$—, (—NR)S(=O)$_2$—, —SS(=O)—, —OS(=O)—,
(NR)S(=O)—, —SS(=O)$_2$—, (—S)$_2$P(=O)—, —(—S)P(=O)—,
—P(=O)(-)$_2$, (—S)$_2$P(=S)—, —(—S)P(=S)—, —P(=S)(-)$_2$,
(—NR)$_2$P(=O)—, (—NR)(—S)P(=O)—, (—O)(—NR)P(=O)—,
(—O)(—S)P(=O)—, (—O)$_2$P(=O)—, —(—O)P(=O)—, —(—NR)P(=O)—, (—NR)₂P(=S)—, (—NR)(—S)P(=S)—, (—O)(—NR)P(=S)—,
(—O)(—S)P(=S)—, (—O)₂P(=S)—, —(—O)P(=S)— or —(—NR)P(=S)—, in each of these groups the atom (D) is doubly bonded to the heteroatom (E), which in turn is bonded to the sulfur atom (S), which is coupled to the silicon atom (Si) by means of a group (G), $R^1$ mutually independently denotes H,
a straight, cyclic or branched alkyl chain, preferably ($C_1$–$C_{18}$) alkyl, particularly preferably ($C_1$–$C_4$) alkyl, optionally alkyl chains containing unsaturated components such as double bonds (alkenes), triple bonds (alkynes) or alkyl aromatics (aralkyl) or aromatics and displaying the same meanings as in formula (II),
G independently of the other substituents denotes hydrogen, a straight, cyclic or branched alkyl chain with ($C_1$–$C_{18}$), whereby the alkyl chains can optionally contain an unsaturated component, such as double bonds (alkenes), triple bonds (alkynes) or alkyl aromatics (aralkyl) or aromatics, if p=0 in formula (IV), G is preferably hydrogen (H), G does not correspond to the structure of an α,β-unsaturated fragment that is bonded to the Y fragment in such a way that an α,β-unsaturated thiocarbonyl fragment is formed, $X^1$, $X^2$ and $X^3$ each mutually independently has the meaning as in formula (I).

An index p of 0 to 2 is preferred, whereby $X^1$, $X^2$ or $X^3$ is an RO— or RC(=O)O—. A fragment with p=0, $X^1$, $X^2$ or $X^3$=ethoxy and with G=alkyl skeleton or substituted alkyl skeleton with $C_3$ to $C_{12}$ is particularly preferred. At least one X does not have to be equal to —$R^1$.

In (Q)₂D(=E)Q can be oxygen, sulfur or (—NR—), D can be carbon, sulfur, phosphorus or sulfonyl, E can be oxygen, sulfur or (=$NR^1$).

Preferred examples of the function (—YS—) in formulae (IV) and (V) are:
thiocarboxylate esters —C(=O)—S—, dithiocarboxylates —C(=S)—S—, thiocarbonate esters —O—C(=O)—S—, dithiocarbonate esters —S—C(=O)—S— and —O—C(=S)—S—, trithiocarbonate esters —S—C(=S)—S—, dithiocarbamate esters —N—C(=S)—S—, thiosulfonate esters —S(=O)₂—S—, thiosulfate esters —O—S(=O)₂—S—, thiosulfamate esters (—N—)S(=O)₂—S—, thiosulfinate esters —C—S(=O)—S—, thiosulfite esters —O—S(=O)—S—, thiosulfimate esters N—S(=O)—S—, thiophosphate esters P(=O)(O—)₂(S—), dithiophosphate esters P(=O)(O—)(S—)₂ or P(=S)(O—)₂(S—), trithiophosphate esters P(=O)(S—)₃ or P(=S)(O—)(S—)₂, tetrathiophosphate esters P(=S)(S—)₃, thiophosphamate esters —P(=O)(—N—)(S—), dithiophosphamate esters —P(=S)(—N—)(S—), thiophosphoramidate esters (—N—)P(=O)(O—)(S—), dithiophosphoramidate esters (—N—)P(=O)(S—)₂ or (—N—)P(=S)(O—)(S—) or trithiophosphoramidate esters (—N—)P(=S)(S—)₂.

The following compounds can be used for example as the silane having the general formula (IV) or (V):
2-triethoxysilyl-1-ethyl thioacetate, 2-trimethoxysilyl-1-ethyl thioacetate, 2-(methyldimethoxysilyl)-1-ethyl thioacetate, 3-trimethoxysilyl-1-propyl thioacetate, triethoxysilyl methyl thioacetate, trimethoxysilyl methyl thioacetate, triisopropoxysilyl methyl thioacetate, methyl diethoxysilyl methyl thioacetate, methyl dimethoxysilyl methyl thioacetate, methyl diisopropoxysilyl methyl thioacetate, dimethyl ethoxysilyl methyl thioacetate, dimethyl methoxysilyl methyl thioacetate, dimethyl isopropoxysilyl methyl thioacetate, 2-triisopropoxysilyl-1-ethyl thioacetate, 2-(methyl diethoxysilyl)-1-ethyl thioacetate, 2-(methyl diisopropoxysilyl)-1-ethyl thioacetate, 2-(dimethylethoxysilyl)-1-ethyl thioacetate, 2-(dimethyl methoxysilyl)-1-ethyl thioacetate, 2-(dimethyl isopropoxysilyl)-1-ethyl thioacetate, 3-triethoxysilyl-1-propyl thioacetate, 3-triisopropoxysilyl-1-propyl thioacetate, 3-methyl diethoxysilyl-1-propyl thioacetate, 3-methyl dimethoxysilyl-1-propyl thioacetate, 3-methyl diisopropoxysilyl-1-propyl thioacetate, 1-(2-triethoxysilyl-1-ethyl)-4-thioacetyl cyclohexane, 1-(2-triethoxysilyl-1-ethyl)-3-thioacetyl cyclohexane, 2-triethoxysilyl-5-thioacetyl norbornene, 2-triethoxysilyl-4-thioacetyl norbornene, 2-(2-triethoxysilyl-1-ethyl)-5-thioacetyl norbornene, 2-(2-triethoxysilyl-1-ethyl)-4-thioacetyl norbornene, 1-(1-oxo-2-thia-5-triethoxysilylpentyl) benzoic acid, 6-triethoxysilyl-1-hexyl thioacetate, 1-triethoxysilyl-5-hexyl thioacetate, 8-triethoxysilyl-1-octyl thioacetate, 1-triethoxysilyl-7-octyl thioacetate, 6-triethoxysilyl-1-hexyl thioacetate, 1-triethoxysilyl-5-octyl thioacetate, 8-trimethoxysilyl-1-octyl thioacetate, 1-trimethoxysilyl-7-octyl thioacetate, 10-triethoxysilyl-1-decyl thioacetate, 1-triethoxysilyl-9-decyl thioacetate, 1-triethoxysilyl-2-butyl thioacetate, 1-triethoxysilyl-3-butyl thioacetate, 1-triethoxysilyl-3-methyl-2-butyl thioacetate, 1-triethoxysilyl-3-methyl-3-butyl thioacetate, 3-trimethoxysilyl-1-propyl thiooctoate, 3-triethoxysilyl-1-propyl thiopalmitate, 3-triethoxysilyl-1-propyl thiooctoate, 3-triethoxysilyl-1-propyl thiobenzoate, 3-triethoxysilyl-1-propyl thio-2-ethyl hexanoate, 3-methyl diacetoxysilyl-1-propyl thioacetate, 3-triacetoxysilyl-1-propyl thioacetate, 2-methyl diacetoxysilyl-1-ethyl thioacetate, 2-triacetoxysilyl-1-ethyl thioacetate, 1-methyl diacetoxysilyl-1-ethyl thioacetate or 1-triacetoxysilyl-1-ethyl thioacetate.

Compounds having the formulae IV and V are also described in EP0958298 or WO9909036 which are relied on and incorporated herein for that purpose.

An organosilicon compound or a mixture of organosilicon compounds having the general formula (VI)

can be used as the silane, whereby $X^1$, $X^2$, $X^3$ and A, each mutually independently, have the meaning according to formula (I) and Sub is
—SH, —NH₂, —NH(A-Si$X^1X^2X^3$), —N(A-Si$X^1X^2X^3$)₂, O—C(O)—CMe=CH₂ or —SCN.

The following compounds can be used for example as the silane having the general formula (VI):

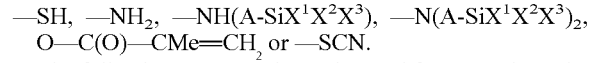

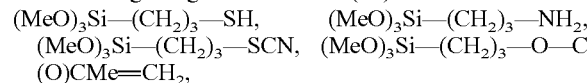

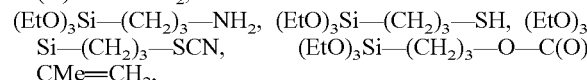

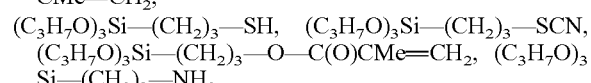

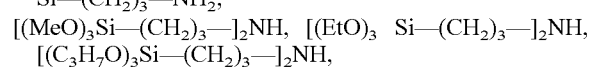

or

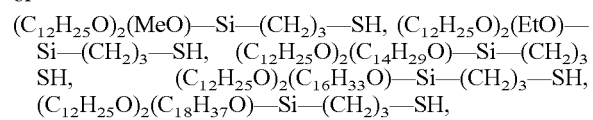

$(C_{14}H_{29}O)_2(MeO)$—Si—$(CH_2)_3$—SH, $(C_{14}H_{29}O)_2(EtO)$—Si—$(CH_2)_3$—SH, $(C_{14}H_{29}O)_2(C_{12}H_{25}O)$—Si—$(CH_2)_3$—SH, $(C_{14}H_{29}O)_2(C_{16}H_{33}O)$—Si—$(CH_2)_3$—SH, $(C_{14}H_{29}O)_2(C_{18}H_{37}O)$—Si—$(CH_2)_3$—SH,
$(C_{16}H_{33}O)_2(MeO)$—Si—$(CH_2)_3$—SH, $(C_{16}H_{33}O)_2(EtO)$—Si—$(CH_2)_3$—SH, $(C_{16}H_{33}O)_2(C_{12}H_{25}O)$—Si—$(CH_2)_3$—SH, $(C_{16}H_{33}O)_2(C_{14}H_{29}O)$—Si—$(CH_2)_3$—SH, $(C_{16}H_{33}O)_2(C_{18}H_{37}O)$—Si—$(CH_2)_3$—SH,
$(C_{18}H_{37}O)_2(MeO)$—Si—$(CH_2)_3$—SH, $(C_{18}H_{37}O)_2(EtO)$—Si—$(CH_2)_3$—SH, $(C_{18}H_{37}O)_2(C_{12}H_{25}O)$—Si—$(CH_2)_3$—SH, $(C_{18}H_{37}O)_2(C_{14}H_{29}O)$—Si—$(CH_2)_3$—SH, $(C_{18}H_{37}O)_2(C_{16}H_{33}O)$—Si—$(CH_2)_3$—SH, or $(C_{12}H_{25}O)_2(MeO)$—Si—$(CH_2)_3$—$NH_2$, $(C_{12}H_{25}O)_2(EtO)$—Si—$(CH_2)_3$—$NH_2$, $(C_{12}H_{25}O)_2(C_{14}H_{29}O)$—Si—$(CH_2)_3$—$NH_2$, $(C_{12}H_{25}O)_2(C_{16}H_{33}O)$—Si—$(CH_2)_3$—$NH_2$, $(C_{12}H_{25}O)_2(C_{18}H_{37}O)$—Si—$(CH_2)_3$—$NH_2$,
$(C_{14}H_{29}O)_2(MeO)$—Si—$(CH_2)_3$—$NH_2$, $(C_{14}H_{29}O)_2(EtO)$—Si—$(CH_2)_3$—$NH_2$, $(C_{14}H_{29}O)_2(C_{12}H_{25}O)$—Si—$(CH_2)_3$—$NH_2$, $(C_{14}H_{29}O)_2(C_{16}H_{33}O)$—Si—$(CH_2)_3$—$NH_2$, $(C_{14}H_{29}O)_2(C_{18}H_{37}O)$—Si—$(CH_2)_3$—$NH_2$,
$(C_{16}H_{33}O)_2(MeO)$—Si—$(CH_2)_3$—$NH_2$, $(C_{16}H_{33}O)_2(EtO)$—Si—$(CH_2)_3$—$NH_2$, $(C_{16}H_{33}O)_2(C_{12}H_{25}O)$—Si—$(CH_2)_3$—$NH_2$, $(C_{16}H_{33}O)_2(C_{14}H_{29}O)$—Si—$(CH_2)_3$—$NH_2$, $(C_{16}H_{33}O)_2(C_{18}H_{37}O)$—Si—$(CH_2)_3$—$NH_2$,
$(C_{18}H_{37}O)_2(MeO)$—Si—$(CH_2)_3$—$NH_2$, $(C_{18}H_{37}O)_2(EtO)$—Si—$(CH_2)_3$—$NH_2$, $(C_{18}H_{37}O)_2(C_{12}H_{25}O)$—Si—$(CH_2)_3$—$NH_2$, $(C_{18}H_{37}O)_2(C_{14}H_{29}O)$—Si—$(CH_2)_3$—$NH_2$, $(C_{18}H_{37}O)_2(C_{16}H_{33}O)$—Si—$(CH_2)_3$—$NH_2$, or $(C_{12}H_{25}O)_2(C_{14}H_{29}O)$—Si—$(CH_2)_3$—SCN, $(C_{12}H_{25}O)_2(C_{16}H_{33}O)$—Si—$(CH_2)_3$—SCN,
$(C_{12}H_{25}O)_2(C_{18}H_{37}O)$—Si—$(CH_2)_3$—SCN, $(C_{14}H_{29}O)_2(C_{12}H_{25}O)$—Si—$(CH_2)_3$—SCN,
$(C_{14}H_{29}O)_2(C_{16}H_{33}O)$—Si—$(CH_2)_3$—SCN, $(C_{14}H_{29}O)_2(C_{18}H_{37}O)$—Si—$(CH_2)_3$—SCN,
$(C_{16}H_{33}O)_2(C_{12}H_{25}O)$—Si—$(CH_2)_3$—SCN, $(C_{16}H_{33}O)_2(C_{14}H_{29}O)$—Si—$(CH_2)_3$—SCN,
$(C_{16}H_{33}O)_2(C_{18}H_{37}O)$—Si—$(CH_2)_3$—SCN, $(C_{18}H_{37}O)_2(C_{12}H_{25}O)$—Si—$(CH_2)_3$—SCN,
$(C_{18}H_{37}O)_2(C_{14}H_{29}O)$—Si—$(CH_2)_3$—SCN, $(C_{18}H_{37}O)_2(C_{16}H_{33}O)$—Si—$(CH_2)_3$—SCN, or $(C_{12}H_{25}O)_2(MeO)$—Si—$(CH_2)_3$—O—C(O)CMe=$CH_2$, $(C_{12}H_{25}O)_2(EtO)$—Si—$(CH_2)_3$—O—C(O)CMe=$CH_2$,
$(C_{14}H_{29}O)_2(MeO)$—Si—$(CH_2)_3$—O—C(O)CMe=$CH_2$, $(C_{14}H_{29}O)_2(EtO)$—Si—$(CH_2)_3$—O—C(O)CMe=$CH_2$,
$(C_{16}H_{33}O)_2(MeO)$—Si—$(CH_2)_3$—O—C(O)CMe=$CH_2$, $(C_{16}H_{33}O)_2(EtO)$—Si—$(CH_2)_3$—O—C(O)CMe=$CH_2$,
$(C_{18}H_{37}O)_2(MeO)$—Si—$(CH_2)_3$—O—C(O)CMe=$CH_2$, $(C_{18}H_{37}O)_2(EtO)$—Si—$(CH_2)_3$—O—C(O)CMe=$CH_2$, or $[(C_yH_{2y+1}O)(EtO)_2Si(CH_2)_3]$—$NH_2$, $[(C_yH_{2y+1}O)_2(EtO)Si(CH_2)_3]$—$NH_2$,
$[(C_yH_{2y+1}O)(EtO)_2Si(CH_2)_3]$—SH, $[(C_yH_{2y+1}O)_2(EtO)Si(CH_2)_3]$—SH, $[(C_yH_{2y+1}O)(EtO)_2Si(CH_2)_3]$—SCN, $[(C_yH_{2y+1}O)_2(EtO)Si(CH_2)_3]$—SCN, $[(C_yH_{2y+1}O)(EtO)_2Si(CH_2)_3]$—O—C(O)—CMe=$CH_2$,
$[(C_yH_{2y+1}O)_2(EtO)Si(CH_2)_3]$—O—C(O)—CMe=$CH_2$,
where y=10–24, or mixtures of the aforementioned silanes.

Oligomers, in other words oligosiloxanes and polysiloxanes, or cooligomers of silanes having the general formula (I)–(VI), or mixtures thereof, can be used as the silane. The siloxanes can be obtained by oligomerization or cooligomerization of the corresponding silane compounds having the general formulae (I)–(VI) by addition of water and of additives known to the person skilled in the art in this area.

Oligomeric silanes are described for example in EP 652 245 B1, EP 0 700 951 B1, EP 0 978 525 A2 and DE 199 29 021 A1 which are relied in and incorporated herein by reference for the disclosure of oligomeric silanes.

Mixtures of silanes can also be used as the silane within the meaning of the present invention for the modification of fillers, for example mixtures of silanes having the general formula (I)–(VI) or mixtures of the oligomeric or polymeric siloxanes of silanes having the general formula (I)–(VI) or mixtures of silanes having the general formula (I)–(VI) with mixtures of the oligomeric or polymeric siloxanes of silanes having the general formula (I)–(VI).

A natural and/or synthetic filler can be used as the untreated microbeaded or microgranular oxidic or siliceous filler.

The microbeaded or microgranular oxidic or siliceous filler can be compatible with the rubbers and display the fine-particle character and reinforcing effect in the polymer matrix that is necessary for this application.

Silicates, for example kaolin, mica, kieselguhr, diatomaceous earth, talc, wollastonite or clay, as well as silicates inter alia in the form of glass beads, ground glass chips (glass powder), glass fibres or glass cloths, can be used as the natural, siliceous filler.

All types of metal oxides, for example aluminum oxide, aluminum hydroxide or trihydrate, zinc oxide, boron oxides, magnesium oxides, as well as transition metal oxides, such as titanium dioxide, can be used as oxidic fillers.

In addition, aluminum silicates, silicates, zeolites, precipitated silicas with BET surface areas (measured with gaseous nitrogen) of 1 to 1000 $m^2/g$, preferably to 300 $m^2/g$, can be used as the oxidic or siliceous filler.

By way of example, the precipitated silica Ultrasil 7005 sold by Degussa AG as well as the silica Hi-Sil® 210 sold by PPG Industries Inc. and the products Zeosil 1115 MP, Zeosil 1135 MP, Zeosil 1165 MP, Zeosil 1165 MPS or Zeosil 1205 MP sold by Rhodia can be used.

Silicas from other manufacturers that display similar properties or product characteristics to the silicas mentioned above or display similar, comparable analytical data (especially BET surface areas, CTAB surface areas, BET/CTAB ratio, Sears number, bead fraction or particle size distributions, shape factors, circle factors and DBP index), can also be used without any problem to produce the silane-modified oxidic or siliceous filler according to the invention.

Compounds that are gaseous under normal temperature and pressure conditions and that are suitable as a reaction matrix for the silane/filler mixtures can be used as the compressed gas. For example, carbon dioxide, helium, nitrogen, dinitrogen monoxide, sulfur hexafluoride, gaseous alkanes with 1 to 5 C atoms (methane, ethane, propane, n-butane, isobutane, neopentane), gaseous alkenes with 2 to 4 C atoms (ethylene, propylene, butene), gaseous alkynes (acetylene, propyne and butyne-1), gaseous dienes (propadiene), gaseous fluorocarbons, chlorinated hydrocarbons and/or chlorofluorocarbons (freons, CHCs, HCFCs) or substitutes thereof that are used because of current legislation, or ammonia, as well as mixtures of these substances, can be used.

Carbon dioxide can preferably be used as the compressed gas, since it is non-toxic, non-combustible, unreactive and inexpensive. In addition, the necessary supercritical conditions or near critical conditions can easily be achieved as the critical pressure and critical temperature are only 73 bar and 31° C. respectively.

Compressed gases can be defined according to E. Stahl, K. W. Quirin, D. Gerard, "Verdichtete Gase zur Extraktion und Raffination", Springer-Verlag, page 12–13. Compressed gases can be supercritical gases, critical gases or gases in the liquefied region.

Surprisingly, the use according to the invention of a compressed gas is extremely advantageous. Commercial microbeaded or microgranular, oxidic or siliceous fillers corresponding to the present invention, for example, and especially silicas, are silanized unexpectedly well, not only at or adjacent to the surface but also comparatively homogeneously within a microbead or microgranule.

Due to the high dissolving power and diffusibility, the low viscosity and the ability of organic silanes or organic oligomeric or polymeric siloxanes in particular to permit high diffusion rates in the compressed gas, compressed gases are surprisingly suitable for impregnating microporous, mesoporous and macroporous solids with monomeric or oligomeric silane compounds. The silane compounds can be transported by the compressed gas into the pores and channels and onto the so-called "inner surfaces" of the microbeaded or microgranular porous fillers. They are then chemically or/and physically bonded there and immobilized.

Since they are in gaseous form under normal conditions, compressed gases can advantageously be easily separated from the filler on completion of its silanization and in the case of carbon dioxide in particular they also have virtually no environmentally hazardous potential, since they find their way into the natural carbon cycle or can easily be recycled. That is a significant technical advantage as compared with known processes, since on the one hand a homogeneous reaction matrix is assured by the compressed fluid in the same way as with known organic solvents yet at the same time a complex removal step, for example removal of a solvent in vacuo under thermal loading, can be avoided.

The compressed gas can be pressurized in an air-tight sealed room or container in which the material to be treated is located. During this process the pressure can be increased, generally from atmospheric pressure, to the operating pressure for the process according to the invention.

The silanes used can be present in the compressed gas in undissolved, partially dissolved or wholly dissolved form.

The microbeaded or microgranular, oxidic or siliceous filler and the silane can first be mixed together or brought into contact and then mixed or brought into contact with the gas in compressed form.

The microbeaded or microgranular, oxidic or siliceous filler can first be mixed together with the gas, or brought into contact with the gas in compressed form and then mixed or brought into contact with the silane.

The silane can first be mixed together or brought into contact with the gas in compressed form and then mixed or brought into contact with the corresponding microbeaded or microgranular, oxidic or siliceous filler.

"Brought into contact" can mean that the cited material is immersed, wetted or covered and is dissolved or undissolved, suspended, adsorbed or absorbed.

The "bringing into contact" can be achieved for example in a container or in a hermetically sealed room into which the unmodified filler, the silane component and the gas that can potentially be transformed into the compressed state are introduced by suitable means.

Contact between the unmodified filler and the silane component can be achieved here by means of various technical solutions. This can preferably be achieved using a suitable mixing unit with an integral liquid metering device, such as are very familiar to the person skilled in the art in this field. These can be, by way of example but not exclusively, mixers such as are supplied by such companies are Drais, Eirich, Forberg, Gericke, Lödige, and Ruberg.

The mixing unit can provide a homogeneous, low-abrasion distribution of the silane used onto the microbeaded or microgranular, oxidic or siliceous filler. The energy input can advantageously be low. Tumbling mixers (e.g. drum mixers) and mixers with rotating tools and low particle loading (Froude number <1) can be used for this purpose.

Contact between the homogeneously mixed silane and filler component and the gas which can potentially be transformed into the compressed state can be established for example in a container or in a hermetically sealed room into which the mixture of filler and silane can be introduced by suitable means. "Establishing contact" can mean that the cited material is immersed in the impregnating fluid and is wetted and covered by it, preferably that the microbeaded or microgranular, oxidic or siliceous filler is completely immersed, or that all outer and inner surfaces of the microbeaded or microgranular, oxidic or siliceous filler are in contact with the compressed gas.

The solubility of the silane component in the compressed gas can be dependent on the nature of said gas, on its pressure and temperature. It can also be modulated and optimized by varying the pressure and temperature in order to adjust the physical properties of the compressed gas. In some cases the concentration of the silane in the solution used as the reaction medium can influence the efficiency of the treatment.

In the process according to the invention 10–250 parts by weight of microbeaded or microgranular, oxidic or siliceous filler can be reacted with 0.1–50 parts by weight, preferably 0.5–15 parts by weight, of silane.

In the process according to the invention the pressure, which is also known as the operating pressure, can generally be between 1 and 500 bar, preferably between 1 and 200 bar, particularly preferably between 1 and 150 bar.

The temperature (operating temperature) at which the process can be performed is between 0 and 300° C., preferably between 0 and 200° C., particularly preferably between 0 and 130° C.

The reaction can be performed in a typical reaction vessel for high temperature/high pressure reactions or high pressure extractions which are well known in the art.

During the modification the pressure can be kept constant at various pressure levels for periods of 5–720 min, preferably 5–240 min, particularly preferably 5–30 min, and during this time the filler can be immersed or stirred in the compressed gas or the compressed gas can be passed through it.

Additives can be added to the microbeaded or microgranular, oxidic or siliceous filler and/or silane before the reaction in the compressed gas.

The silane-modified oxidic or siliceous filler can be brought into contact with additional additives during the reaction in the compressed gas.

During the reaction of the microbeaded or microgranular, oxidic or siliceous filler in the compressed gas, additional additives can be introduced into the incoming or outgoing stream of compressed gas flowing through the silane-modified oxidic or siliceous filler.

Ammonia, sulfur dioxide, water, short-chain or long-chain alcohols, for example methanol, ethanol, propanol, butanol, dodecanol, tetradecanol, hexadecanol, octadecanol or other alcohols with molecular weights >50 g/mol, short-chain or long-chain polyethers or polyether alcohols, for example diethylene glycol, triethylene glycol or others with molecular weights >100 g/mol, short-chain or long-chain amines with molecular weights >50 g/mol, emulsifiers or short-chain or long-chain silicone oils, for example silicone oils with molecular weights >100 g/mol, or mixtures of the aforementioned compounds, can be used as additives. The silane-modified oxidic or siliceous filler can come into contact with additional substances, in addition to the compressed gas or compressed gas mixtures, during the modification reaction.

The microbeaded or microgranular, oxidic or siliceous filler mixed with the silane can be continuously circulated with a suitable agitator in the high-pressure unit or high-pressure vessel. The stirring speed can be adjusted to the prevailing temperature and pressure.

Lifting agitators, paddle agitators, straight-arm paddle agitators, perforated paddle agitators, cross-arm paddle agitators, anchor agitators, gate agitators, straight-blade turbines, propeller agitators, screw mixers, turbine mixers, disk agitators, planetary-type mixers, centrifugal mixers or impeller agitators can be used as the agitator.

The agitator in the high-pressure vessel can operate at 1–100, preferably 1–50 revolutions, strokes or circulations per minute.

The microbeaded or microgranular, oxidic or siliceous filler mixed with a silane can be continually wetted during the modification reaction by a compressed gas passing through it, without being circulated in the high-pressure vessel or being mixed together any more by agitators.

Following surface modification the silane-modified oxidic or siliceous filler can undergo an evacuation or pressure release stage with separation of the compressed gas and the added additives or part of the added additives from the end product.

The evacuation or pressure release stage can be performed in a time of between 1 min and 180 min, preferably between 1 min and 120 min, particularly preferably between 1 min and 60 min.

The evacuation or pressure release stage can be performed at temperatures between 1 and 300° C., preferably between 1 and 200° C., particularly preferably between 1 and 150° C., and most particularly preferably at temperatures between 1 and 130° C.

The silane-modified oxidic or siliceous filler according to the invention can undergo an additional compacting or processing stage.

The silane-modified oxidic or siliceous filler can be used in paints, lacquers, printing inks, films, coatings, adhesives and lubricants, cosmetics, toothpastes, building auxiliary materials or as a filler in vulcanizable rubbers, silicones or plastics.

The invention also provides rubber compounds that are characterized in that they contain rubber, the silane-modified oxidic or siliceous filler according to the invention, optionally precipitated silica and/or carbon black and/or other rubber auxiliary substances.

Natural rubber or synthetic rubbers can be used to produce rubber compounds according to the invention. Preferred synthetic rubbers are described for example in W. Hofmann, Kautschuktechnologie, Genter Verlag, Stuttgart 1980. They include inter alia polybutadiene (BR), polyisoprene (IR), styrene/butadiene copolymers with styrene contents of 1 to 60, preferably 5 to 50 wt. % (E- or S-SBR), isobutylene/isoprene copolymers (IIR), butadiene/acrylonitrile copolymers with acrylonitrile contents of 5 to 60, preferably 10 to 50 wt. % (NBR), chloroprene (CR), ethylene/propylene/diene copolymers (EPDM), and mixtures of these rubbers.

The rubber compounds according to the invention can contain other rubber auxiliary products, such as for example reaction accelerators and retarders, antioxidants, stabilizers, processing aids, plasticizers, waxes, metal oxides and activators, such as triethanolamine, polyethylene glycol or hexane triol, organically modified silanes and other rubber auxiliary products known to the rubber industry.

The rubber compound can additionally contain alkyl silanes or/and silicone oils.

The rubber auxiliary substances can be used in conventional quantities, which are governed inter alia by the intended application. Conventional quantities are for example quantities of 0.1 to 50 wt. % relative to rubber.

Sulfur, organic sulfur donors or radical formers can serve as crosslinking agents. The rubber compounds according to the invention can additionally contain vulcanization accelerators.

Examples of suitable vulcanization accelerators are mercaptobenzothiazoles, sulfenamides, guanidines, thiurams, dithiocarbamates, thio ureas and thiocarbonates.

The vulcanization accelerators and crosslinking agents can be used in quantities of 0.1 to 10 wt. %, preferably 0.1 to 5 wt. %, relative to rubber.

The rubbers can be mixed with the silane-modified oxidic or siliceous filler according to the invention, optionally with precipitated silica and/or carbon black and/or other rubber auxiliary substances in conventional mixing units, such as rolls, internal mixers and compounding extruders. Such rubber compounds can conventionally be produced in internal mixers, whereby the rubbers, the silane-modified oxidic or siliceous filler according to the invention, optionally the precipitated silica and/or carbon black and/or other rubber auxiliary substances are first incorporated at 100 to 170° C. in one or more successive thermomechanical mixing stages. The sequence in which the individual components are added and the time at which they are added can have a decisive impact on the compound properties obtained. The rubber compound thus obtained can then be mixed with the crosslinking chemicals by known means in an internal mixer or on a roll at 40–110° C. and processed to form what is known as an unvulcanized mix for the subsequent process steps, such as moulding and vulcanization for example.

Vulcanization of the rubber compounds according to the invention can take place at temperatures of 80 to 200° C., preferably 130 to 180° C., optionally under a pressure of 10 to 200 bar.

The rubber compounds according to the invention are suitable for producing rubber mouldings, for example for the production of pneumatic tires for cars and trucks, tire treads for cars and trucks, tire components for cars and trucks, such as e.g. sidewall, liner and carcass, cable sheathing, hoses, drive belts, conveyor belts, roll coverings, bicycle and motor cycle tires and components thereof, shoe soles, sealing rings, profiles and damping elements.

In comparison to purely physical mixtures, for example of bis-(3-triethoxysilylpropyl) tetrasulfide with silica (U.S. Pat. No. 4,076,550), the silane-modified oxidic or siliceous fillers according to the invention display the advantage of good storage stability and hence performance stability. In addition, the fillers according to the invention display a considerably lower content of potentially releasable alcohols, for example methanol or ethanol, than physical mixtures of silanes with fillers, are more readily dispersible and overall display better processing characteristics for users in the rubber processing industry (lower dust content, homogeneous compounding, reduction in mixing stages and mixing times, compounds with stable properties after the first mixing stage).

In comparison to known silane-modified fillers, for example bis-(3-triethoxysilylpropyl) tetrasulfide on silica (VP Coupsil 8108 from Degussa), the silane-modified oxidic or siliceous fillers according to the invention display the advantage of better storage stability and hence better performance stability. In addition, the fillers according to the invention display in comparison a considerably lower content of potentially releasable alcohol, generally ethanol, are more readily dispersible and overall display better processing characteristics for users in the rubber processing industry (lower dust content, homogeneous compounding, reduction in mixing stages and mixing times). Fewer volatile organic compounds (VOCs) are released during storage.

As compared with the in-situ method and the untreated filler that this method requires, the silane-modified oxidic or siliceous fillers according to the invention have the advantages of an improved water content in the treated filler, a lower moisture absorption and a higher compacted bulk weight, better flow properties and a higher bulk density compared with the untreated filler.

During the mixing process for the in-situ method a chemical reaction must be performed in which optimum process control is required and as a result of which considerable amounts of alcohol are liberated during the silanization reaction. They subsequently escape from the mixture, thereby leading to problems in the exhaust air. This is reduced or avoided by the use of the silane-modified oxidic or siliceous fillers according to the invention.

Microbeaded or microgranular materials mostly have elevated bulk densities, which has a positive impact on the cost effectiveness of transporting the raw material and product. In comparison to powdered silicas, the silanized microbeaded or microgranular fillers according to the invention have similarly advantageous flow and conveying properties to the microbeaded or microgranular fillers used as the starting material.

EXAMPLES

Examples for the Production of Silane-modified Oxidic or Siliceous Fillers According to the Invention The experiments cited below are performed in a high-pressure extraction unit for solids with an autoclave volume of 50 l.

8 kg of Ultrasil 0.7005 precipitated silica (Degussa AG; analytical properties: BET=185 m²/g according to ISO 5794/Annex D, CTAB surface area=173 m²/g, loss on drying=5.5 wt. % (DIN ISO787-2), are physically precoated and mixed together with 640 g Si69 (Degussa AG; bis-(triethoxysilylpropyl) tetrasulfide)) in a Ruberg mixer. In some experiments additional amounts of water are then sprayed onto the mixture of silica and silane.

The silica that is physically precoated with Si69 is introduced into a charging vessel (volume 35 l), which is sealed at the top and bottom with sintering plates. The completely full charging vessel is placed in the autoclave of a high-pressure extraction unit (fixed bed). The autoclave is pressurized using a high-pressure diaphragm pump and defined quantities of carbon dioxide, which is supplied by a high-pressure pump, are passed through at the pressures and temperatures set out in Tables 1–5 for fixed times. Primary reaction refers to the chemical and/or physical immobilization of the silane on the filler. Extraction refers to the partial/complete hydrolysis of the silane and removal of the alcohol. In some examples (Tables 4 and 5) a specific amount of water is metered into the stream of $CO_2$ before it enters the autoclave. In addition, in the examples in Table 5, pressure pulses of between 60 and 100 bar are generated to improve the distribution of the silane on the surface of the silica. After the fixed bed extractor the loaded carbon dioxide is transferred to a separator tank in which it is converted into gaseous form by pressure reduction and/or temperature increase, whereby the solubility for the constituents of the fluid (e.g. extracted ethanol) is reduced and they are largely separated out as a result. After the separator tank the gaseous carbon dioxide is condensed by a condenser and passed to a buffer vessel, from which it can be drawn in again by the high-pressure pump and used for extraction (cyclic process).

In examples 6 to 9 (Table 2) and 10 to 15 (Table 3) the carbon dioxide under the cited pressure and temperature conditions is not transferred to the separator tank but instead is circulated for a certain time by a bypass high-pressure pump, whilst maintaining pressure and temperature, by conveying it in a loop directly back to the autoclave. The stream is only transferred to the separator tank under the cited conditions—as shown in Tables 2+3—to carry out the extraction.

To demonstrate that the throughput direction for production of the filler according to the invention can be varied at will, in Examples 10 to 15 (Table 3) the throughput direction for the carbon dioxide is split, in other words in the cited ratios the carbon dioxide is passed through the autoclave alternately from below and from above, whereby the direction of flow, the throughput of carbon dioxide and the pressure and temperature conditions, as shown in Table 3, are maintained.

TABLE 1

| | | | Primary reaction | | | Extraction | | |
| | | | | | | | | Carbon dioxide |
| Example no. | Silica | Silane coating in phf(Si69) | Pressure in bar | Temperature in ° C. | Time in min | Pressure in bar | Temperature in ° C. | throughput in kg |
| --- | --- | --- | --- | --- | --- | --- | --- | --- |
| 1 | Ultrasil 7005 | 8.8 | 150 | average of 65 | 80 | 270 | average of 90 | 100 |
| 2 | Ultrasil 7005 | 9 | 200 | average of 70 | 80 | 270 | average of 90 | 90 |
| 3 | Ultrasil 7005 | 9.2 | 260 | average of 70 | 80 | 270 | average of 90 | 100 |
| 4 | Ultrasil 7005 | 9.0 | 200 | average of 85 | 80 | 270 | average of 90 | 90 |
| 5 | Ultrasil 7005 | 9.2 | 260 | average of 85 | 80 | 270 | average of 90 | 90 |

TABLE 2

| Example no. | Silica | Silane coating phf (Si69) | Circulation Feed | | | | Primary reaction | | | | Extraction | | | |
|---|---|---|---|---|---|---|---|---|---|---|---|---|---|---|
| | | | Press. in bar | Temp. in °C. | Time in min | CO₂ through-put in kg | Press. in bar | Temp. in °C. | Time in min | CO₂ through-put in kg | Press. in bar | Temp. in °C. | Time in min | CO₂ through-put in kg |
| 6 | Ultrasil 7005 | 9 | 150 | 50 | 50 | 62 | 240 | 90 | 60 | 150 | 270 | 95 | 30 | 80 |
| 7 | Ultrasil 7005 | 9 | 160 | 40 | 50 | 63 | 290 | 90 | 90 | 200 | 270 | 90 | 30 | 90 |
| 8 | Ultrasil 7005 | 9.4 | 150 | 50 | 50 | 120 | 240 | 70 | 30 | 130 | 270 | 90 | 30 | 100 |
| | | | | | | | 240 | 90 | 60 | | | | | |
| 9 | Ultrasil 7005 | 9.4 | 170 | 70 | 50 | 80 | 210 | 90 | 90 | 135 | 270 | 90 | 30 | 100 |

TABLE 3

| Ex. no. | Silane coating phf (Si69) | Circulation Feed | | | | | Primary reaction | | | | | Extraction | | | |
|---|---|---|---|---|---|---|---|---|---|---|---|---|---|---|---|
| | | Press. in bar | Temp. in °C. | Time in min | Through-put direction | CO₂ through-put in kg | Press. in bar | Temp. in °C. | Time in min | Through-put direction | CO₂ through-put in kg | Press. in bar | Temp. in °C. | Time in min | CO₂ through-put in kg |
| 10 | 9.4 | 150 | 50 | 55 | | 140 | 240 | 90 | 30 | ↓ | 60 | 270 | 90 | 30 | 100 |
| | | | | | | | 240 | 90 | 30 | ↑ | 60 | | | | |
| 11 | 9.4 | 150 | 50 | 12 | ↑ | 30 | 240 | 90 | 10 | ↓ | 20 | 270 | 90 | 30 | 100 |
| | | 150 | 50 | 60 | ↓ | 150 | 240 | 90 | 10 | ↑ | 20 | | | | |
| | | | | | | | 240 | 90 | 20 | ↓ | 50 | | | | |
| | | | | | | | 240 | 90 | 20 | ↑ | 50 | | | | |
| 12 | 9.4 | 150 | 50 | 65 | ↓ | 74 | 260 | 95 | 65 | ↑ | 125 | 270 | 95 | 30 | 90 |
| 13 | 9.4 | 150 | 50 | 55 | ↓ | 70 | 290 | 90 | 10 | ↑ | 30 | 270 | 93 | 30 | 90 |
| | | 150 | 50 | 30 | ↑ | 30 | 290 | 90 | 50 | ↓ | 95 | | | | |
| 14 | 9.4 | 150 | 50 | 55 | ↓ | 60 | 240 | 90 | 10 | ↑ | 25 | 270 | 90 | 30 | 90 |
| | | 150 | 50 | 55 | ↑ | 30 | 240 | 90 | 45 | ↓ | 105 | | | | |
| 15 | 9.4 | 150 | 50 | 35 | ↑ | 40 | 150 | 50 | 30 | ↓ | 50 | 270 | 90 | 30 | 90 |
| | | 150 | 50 | 35 | ↓ | 40 | 290 | 90 | 55 | ↑ | 125 | | | | |

TABLE 4

| Example no. | Silica | Silane coating in phf(Si69) | Added water in phf | Addition of water in sc-CO₂ | Pressure in bar | Temperature in °C. | Time in min | Carbon dioxide throughput in kg |
|---|---|---|---|---|---|---|---|---|
| 16 | Ultrasil 7005 | 8 | 0 | | 100 | average of 70 | 10 | |
| Extraction | Ultrasil 7005 | | | +0.2% H₂O rel. to CO₂ | 100 | 80–87 | 60 | 160 kg |
| 17 | Ultrasil 7005 | 8 | 5 | | 100 | average of 70 | 10 | |
| Extraction | Ultrasil 7005 | | | +0.2% H₂O rel. to CO₂ | 100 | 80–87 | 60 | 160 kg |
| 18 | Ultrasil 7005 | 8 | 8 | | 100 | average of 70 | 10 | |
| Extraction | Ultrasil 7005 | | | +0.2% H₂O rel. to CO₂ | 100 | 77–88 | 80 min | 160 kg |

TABLE 5

| | Silica | Silane coating in phf(Si69) | Added water in phf | Addition of water in sc-CO₂ | Pressure in bar | Temperature in °C. | Time in min | Carbon dioxide throughput in kg | Direction of CO₂ feed |
|---|---|---|---|---|---|---|---|---|---|
| 19 | Ultrasil 7005 | 8 | 0 | +0.2% H₂O rel. to CO₂ | 8 pressure pulses between 60 and 100 bar | average of 70 | 150 | | ↓ |
| Extraction | Ultrasil 7005 | | | +0.2% H₂O rel. to CO₂ | 100 | 85 | 60 | 160 kg | ↓ |
| 20 | Ultrasil 7005 | 8 | 5 | +0.2% H₂O rel. to CO₂ | 8 pressure pulses between 60 and 100 bar | average of 70 | 150 | | ↓ |

TABLE 5-continued

| | Silica | Silane coating in phf(Si69) | Added water in phf | Addition of water in sc-$CO_2$ | Pressure in bar | Temperature in ° C. | Time in min | Carbon dioxide throughput in kg | Direction of $CO_2$ feed |
|---|---|---|---|---|---|---|---|---|---|
| Extraction | Ultrasil 7005 | | | +0.2% $H_2O$ rel. to $CO_2$ | 100 | 85 | 60 | 160 kg | ↓ |
| 21 | Ultrasil 7005 | 8 | 8 | +0.2% $H_2O$ rel. to $CO_2$ | 8 pressure pulses between 60 and 100 bar | average of 70 | 150 | | ↓ |
| Extraction | Ultrasil 7005 | | | +0.2% $H_2O$ rel. to $CO_2$ | 100 | 85 | 60 | 160 kg | ↓ |

The Sears numbers are determined by reference to G. W. Sears, Analyt. Chemistry 12 (1956) 1982 according to the following instructions:

Before titration the filler is ground in a mill, whereby it is homogenized and crushed. 60 ml of methanol are added to 2.5 g of the sample thus obtained in a 250 ml titration vessel and as soon as the solid is completely wetted a further 40 ml of water are added to the suspension.

The suspension is dispersed for 30 sec with an agitator (Ultra-Turrax) and then diluted with a further 100 ml of water. The suspension is heated to 25° C. for at least 20 minutes.

Titration is performed as follows on a titroprocessor with a pH electrode (e.g. DL 67, Mettler Toledo with a DG 111 SC electrode):

first stir for 120 sec;

adjust the suspension to pH 6 with 0.1 N potassium hydroxide solution or hydrochloric acid;

add 20 ml NaCl solution (250 g/l);

titrate with 0.1 N KOH from pH 6 to pH 9;

the result is converted to 5 g silica, i.e. to a consumption of 0.1 N KOH in ml per 5 g silica, in order to reach pH 9 from pH 6.

The present determination is a further development, more accurate account and improvement of the method described in G. W. Sears, Analyt. Chemistry 12 (1956) 1982.

The samples are dried for 15–20 h at 105° C. and the BET surface area determined according to DIN 66131 (volumetric method).

The samples were dried for 15–20 h at 105° C. and the micropore volume determined by the t-plot method according to DIN 66135-2.

The samples are dried for 15–20 h at 105° C. and the mesopore distribution determined by the BJH method according to DIN 66134.

The macropore volume (pores of widths >30 or >50 nm) is determined with an Autopore II 9220 mercury porosimeter (Micromeritics) in accordance with the generally known principles and operating instructions in the range up to 400 µm. The samples are first dried for 15–20 h at 105° C. The method serves to determine the pore volume and the pore distribution in porous solids by measuring the volume of mercury pressed in under rising pressure using the method devised by Ritter and Drake according to DIN 66133.

The pore maxima for mesopores and macropores can be read off directly from the corresponding graphs (cumulated intrusion volume (ml/g) and log. differential pore volume dV/dlog D) for the pore volume distribution (ml/g) as a function of the pore diameter (µm).

Determination of the bead distribution and bead fractions by screen analysis is performed as follows:

The bead size distribution of preformed, granular, microgranular or microbeaded silicas is determined. To this end a defined amount of silica is separated with a stack of screens having a varying, standardized mesh width.

The content of the individual bead fractions is determined by weighing. The following equipment is used: mechanical screening machine (Ro-tap); precision balance: accuracy±0.01 g (Mettler)

Standard screens U.S. Standard No. 120, height 25 mm, Ø: 200 mm; mesh widths: 300 µm (50 mesh); 150 µm (100 mesh); 75 µm (200 mesh)

The screens and a receiver are assembled in the specified sequence, in other words with apertures decreasing in size from the top to the bottom. 100 g of the sample to be examined is weighed out using an appropriate scoop. Preselecting the material by pouring or transferring the shaped silica out of the storage vessel should be avoided. After transferring the weighed out silica onto the uppermost screen a cover is placed on top and the stack placed into the screening machine in such a way that a clearance of approx. 1.5 mm remains to enable the screens to rotate freely.

The screens are secured in the machine and then shaken for 5 min—with the vibrator or knocker operating. The screens are then taken apart in turn and the amount of silica contained within each is weighed to an accuracy of 0.1 g. A repeat determination is performed for each sample. The mean of the amounts of silica found in the individual screens and in the receiver is given in % in each case.

The particle size distribution in the samples is determined by laser diffraction analysis without ultrasonic treatment using a Coulter LS 100 with dry powder module (Beckman-Coulter) in accordance with the generally known principles and operating instructions. A continuous stream of original, untreated particles from the sample to be measured is passed in an air jet through a laser beam for 60 sec. The stream of particles is penetrated by the laser and the various particle sizes are detected and evaluated statistically. The minimum and maximum particle sizes that can be measured are 0.4 µm and 900 µm respectively.

Determination of the particle size distribution after ultrasonic treatment (degradation behaviour of the samples) is performed by laser diffraction analysis using a Coulter LS 100 with microvolume module (Beckman-Coulter) in accordance with the generally known principles and operating instructions after the sample has been predispersed in ethanol and treated for 60 sec. in a closed screw-cap jar in an ultrasonic bath (US bath RK100, Bandelin). The minimum and maximum particle sizes that can be measured are 0.4 µm and 900 µm respectively.

In order to determine the average sulfur content in the samples, samples are taken from the autoclave trays at both ends of the tray and in the middle, and their sulfur content determined by known methods by:

Schöniger digestion in an oxygen atmosphere (cf. F. Ehrenberger, S. Gorbauch, "Methoden der organischen Elementar- und Spurenanalyse", Verlag Chemie GmbH, Weinheim/Bergstraβe, 1973) and subsequent ion-chromatographic analysis (ion chromatograph 690 from Metrohm; PRP X-100 column from Hamilton; mobile solvent: 2 mmol salicylate buffer, pH 7) according to DIN ISO 10304-2.

The average sulfur content in the overall sample is then obtained as the arithmetic mean of the 3 values for individual samples determined in this way.

The water content in the samples is determined as follows:

10 g of the silanized silica are crushed for 15 seconds in a coffee grinder and the water content is then determined in accordance with the known principles that are familiar to the person skilled in the art using a Karl Fischer titrator (Metrohm, 720 KFS Titrino) and the Karl Fischer titration chemicals no. 1.09241, no. 1.09243 and no. 1.06664 (disodium tartrate dihydrate) available from Merck.

The carbon content in the samples is determined by known standard methods using a CS-244 carbon/sulfur determinator from LECO.

By reference to the procedure described in Kautschuk, Gummi, Kunststoffe 51, (1998) 525 by Hunsche et al. the residual alcohol (ethanol) on the filler is determined as follows:

10 ml diethylene glycol monobutyl ether (DEGMBE) and 0.3 ml 0.5 mol/l $H_2SO_4$ are added to 1 g of the filler according to the invention in a glass ampoule that is closed with a tight-fitting cap after being filled. The mixture is thoroughly mixed in the glass ampoule for 20 min at 60° C. in a water bath. 10 ml decane are then added to the mixture, the temperature of which has been rapidly adjusted to 25° C. Appropriate amounts are then removed from the thoroughly mixed organic phase for HPLC analysis (HPLC device with Jasco 851-AS autosampler, Jasco PU 980 pump, 7515A RI detector; TiO2 column, 250×4.5 mm, 5 μm, YMC; mobile phase: DEGMBE with cyclohexane; temperature 25° C.) on ethanol.

The shape factor and circle factor of the samples is determined as follows:

REM analyses of pulverized powders of the fillers according to the invention are performed on a Jeol JSM 6400 scanning electron microscope and analyzed on-line using the image analysis software Analysis 3.2 from SIS (soft imaging software) in accordance with the conventional principles and procedures known to the person skilled in the art:

Circle Factor (FCIRCLE)

The circle factor (FCIRCLE) indicates by how much the particle shape differs from the ideal circular shape.

$$FCIRCLE = \frac{4\pi(\text{Area})}{P^2}$$

(1.0 for circular, <1 for oblong or branched aggregates)

Area=area of a particle, calculated from the number of pixels that fall on a particle and the partial area of one pixel P=perimeter (i.e. the circumference of the more or less complex particle)

Shape Factor (FSHAPE)

$$\text{Shape factor } FSHAPE = \frac{DMIN}{DMAX}$$

The shape factor (FSHAPE) indicates by how much the particle shape differs from the ideal circular shape by considering 2 possible diameters of a particle (D min, D max).

(1.0 for circular and other exactly isometric aggregates, <1 for oblong aggregates)

D MIN=minimum diameter of a particle under consideration

D MAX=maximum diameter of the same particle under consideration

TABLE 6

| Example no. | Average ethanol content μmol/g | Sears numbers | BET surface area m²/g | Micropores, (d < 2 nm) ml/g | Mesopore volume, (d = 2–30 nm) ml/g | Mesopore volume, (d = 2–50 nm) ml/g | Pore maximum, mesopores nm | Macropores, volume, (d > 30 nm) ml/g | Macropores, volume, (d > 50 nm) ml/g | Pore maximum, macropores μm | Water content in wt. % | Carbon content in wt. % | Sulfur content (average) in wt. % |
|---|---|---|---|---|---|---|---|---|---|---|---|---|---|
| Ultrasil 7005 | 0 | 23.9 | 185 ± 3 | 0.02 ± 0.01 | 0.41 ± 0.03 | 0.87 ± 0.06 | 19 ± 4 | 3.26 ± 0.2 | 2.91 ± 0.2 | 130 ± 10 | 6.7 | 0.06 | 0.2 |
| 1 | 412 | 20.5 | 144 ± 3 | <0.01 | 0.36 ± 0.03 | 0.79 ± 0.06 | 18 ± 4 | 2.89 ± 0.2 | 2.59 ± 0.2 | 110 ± 10 | 2.64 | 2.15 | 1.7 |
| 2 | 428 | 20.1 | 140 ± 3 | <0.01 | 0.33 ± 0.02 | 0.74 ± 0.06 | 17 ± 4 | 2.85 ± 0.2 | 2.56 ± 0.2 | 120 ± 10 | 2.15 | 2.45 | 1.8 |
| 3 | 440 | 21.7 | 149 ± 3 | <0.01 | 0.35 ± 0.02 | 0.77 ± 0.06 | 18 ± 4 | 2.90 ± 0.2 | 2.60 ± 0.2 | 100 ± 10 | 2.38 | 2.30 | 1.75 |
| 4 | 458 | 12.9 | 145 ± 3 | <0.01 | 0.39 ± 0.03 | 0.82 ± 0.06 | 18 ± 4 | 2.81 ± 0.2 | 2.53 ± 0.2 | 150 ± 10 | 2.07 | 2.55 | 1.95 |
| 5 | 463 | 13.3 | 144 ± 3 | <0.01 | 0.37 ± 0.03 | 0.77 ± 0.06 | 17 ± 4 | 2.89 ± 0.2 | 2.58 ± 0.2 | 120 ± 10 | 2.00 | 2.50 | 1.95 |

TABLE 6.1

Particle size distribution using a Coulter LS 100 with microvolume module after ultrasonic treatment (X % of the articles are larger than Y μm)

| Example no. | Mean value μm | Median value μm | Maximum μm | X = 5% Y μm | X = 10% Y μm | X = 50% Y μm | X = 90% Y μm | X = 95% Y μm | Bead size distribution by screen analysis | | | |
|---|---|---|---|---|---|---|---|---|---|---|---|---|
| | | | | | | | | | >300 μm | 150–300 μm | 75–150 μm | <75 μm |
| Ultrasil 7005 | 347.7 | 338.8 | 361.8 | 624.8 | 551.8 | 338.8 | 169.3 | 81.80 | 73.5 | 23.7 | 2.6 | 0.1 |
| 1 | 37.61 | 34.46 | 47.19 | 80.46 | 70.48 | 34.46 | 10.17 | 7.25 | 61.3 | 37.5 | 0.8 | 0.4 |
| 2 | 59.17 | 46.27 | 58.48 | 16.40 | 120 | 46.27 | 11.19 | 7.75 | 75.1 | 20.7 | 4 | 0.2 |
| 3 | 34.12 | 31.40 | 42.39 | 72.05 | 62.65 | 31.40 | 9.97 | 7.13 | 72.9 | 23.2 | 3.6 | 0.2 |
| 4 | 44.20 | 37.12 | 52.53 | 106.9 | 89.60 | 37.12 | 10.16 | 7.15 | 71.5 | 25.4 | 3 | 0.2 |
| 5 | 36.98 | 34.12 | 47.19 | 78.95 | 68.67 | 34.12 | 9.96 | 7.03 | 51.3 | 46.7 | 1.5 | 0.5 |

TABLE 7

| Example no. | Average ethanol content μmol/g | Sears numbers | BET surface area m²/g | Micropores, (d < 2 nm) ml/g | Mesopore volume, (d = 2–30 nm) ml/g | Mesopore volume, (d = 2–50 nm) ml/g | Pore maximum, mesopores nm | Macropores, volume, (d > 30 nm) ml/g | Macropores, volume, (d > 50 nm) ml/g | Pore maximum, macropores nm | Water content in wt. % | Carbon content in wt. % | Sulfur content (average) in wt. % |
|---|---|---|---|---|---|---|---|---|---|---|---|---|---|
| Ultrasil 7005 | 0 | 23.9 | 185 ± 3 | 0.02 ± 0.01 | 0.41 ± 0.03 | 0.87 ± 0.06 | 19 ± 4 | 3.26 ± 0.2 | 2.91 ± 0.2 | 130 ± 10 | 6.7 | 0.06 | 0.2 |
| 6 | 399 | 21.7 | 140 ± 3 | <0.01 | 0.35 ± 0.02 | 0.75 ± 0.06 | 20 ± 4 | 2.81 ± 0.2 | 2.46 ± 0.1 | 90 ± 10 | 3.29 | 2.00 | 2.2 |
| 7 | 402 | 19.5 | 142 ± 3 | <0.01 | 0.33 ± 0.02 | 0.68 ± 0.06 | 20 ± 4 | 2.79 ± 0.2 | 2.45 ± 0.1 | 90 ± 10 | 3.26 | 2.10 | 1.9 |
| 8 | 435 | 20.7 | 140 ± 3 | <0.01 | 0.35 ± 0.02 | 0.73 ± 0.06 | 20 ± 4 | 2.83 ± 0.2 | 2.47 ± 0.1 | 90 ± 10 | 3.16 | 2.20 | 2.1 |
| 9 | 282 | 16.2 | 155 ± 3 | 0.01 ± 0.01 | 0.36 ± 0.02 | 0.76 ± 0.06 | 20 ± 4 | 3 ± 0.2 | 2.63 ± 0.2 | 130 ± 20 | 3.79 | 1.73 | 2.0 |

TABLE 7.1

Particle size distribution using a Coulter LS 100 with microvolume module after ultrasonic treatment (X % of the particles are larger than Y μm)

| Example no. | Mean value μm | Median value μm | Maximum μm | X = 5% Y μm | X = 10% Y μm | X = 50% Y μm | X = 90% Y μm | X = 95% Y μm | Bead size distribution by screen analysis | | | |
|---|---|---|---|---|---|---|---|---|---|---|---|---|
| | | | | | | | | | >300 μm | 150–300 μm | 75–150 μm | <75 μm |
| Ultrasil 7005 | 347.7 | 338.8 | 361.8 | 624.8 | 551.8 | 338.8 | 169.3 | 81.80 | 73.5 | 23.7 | 2.6 | 0.1 |
| 6 | 306.9 | 300.5 | 325.0 | 538.0 | 476.6 | 300.5 | 153.5 | 66.17 | 44.7 | 52.3 | 2.3 | 0.6 |
| 7 | 258.3 | 259.8 | 291.9 | 465.8 | 402.0 | 259.8 | 102.6 | 31.30 | 59 | 40 | 1 | 0 |
| 8 | 249.8 | 245.4 | 262.3 | 462.3 | 402.9 | 245.4 | 77.30 | 23.56 | 53.6 | 44.7 | 0.8 | 1 |
| 9 | 213.6 | 208.7 | 235.6 | 410.6 | 356.8 | 208.7 | 70.80 | 18.62 | 50.9 | 47.2 | 1.6 | 0.3 |

TABLE 8

| Example no. | Average ethanol content μmol/g | Sears numbers | BET surface area m²/g | Micropores, (d < 2 nm) ml/g | Mesopore volume, (d = 2–30 nm) ml/g | Mesopore volume, (d = 2–50 nm) ml/g | Pore maximum, mesopores nm | Macropores, volume, (d > 30 nm) ml/g | Macropores, volume, (d > 50 nm) ml/g | Pore maximum, macropores nm | Water content in wt. % | Carbon content in wt. % | Sulfur content (average) in wt. % |
|---|---|---|---|---|---|---|---|---|---|---|---|---|---|
| Ultrasil 7005 | 0 | 23.9 | 185 ± 3 | 0.02 ± 0.01 | 0.41 ± 0.03 | 0.87 ± 0.06 | 19 ± 4 | 3.26 ± 0.2 | 2.91 ± 0.2 | 130 ± 10 | 6.7 | 0.06 | 0.2 |
| 11 | 476 | 21.6 | 138 ± 3 | <0.01 | 0.39 ± 0.03 | 0.86 ± 0.06 | 20 ± 4 | 2.78 ± 0.2 | 2.45 ± 0.1 | 95 ± 10 | 2.90 | 2.10 | 1.9 |
| 12 | 444 | 20.9 | 142 ± 3 | <0.01 | 0.37 ± 0.03 | 0.76 ± 0.06 | 19 ± 4 | 2.80 ± 0.2 | 2.46 ± 0.1 | 100 ± 10 | 2.80 | 2.20 | 1.8 |
| 13 | 505 | 20.3 | 136 ± 3 | <0.01 | 0.38 ± 0.03 | 0.84 ± 0.06 | 19 ± 4 | 2.86 ± 0.2 | 2.54 ± 0.2 | 100 ± 10 | 2.81 | 2.45 | 1.9 |
| 15 | 486 | 21.1 | 138 ± 3 | <0.01 | 0.36 ± 0.02 | 0.76 ± 0.06 | 18 ± 4 | 2.82 ± 0.2 | 2.50 ± 0.2 | 100 ± 10 | 2.79 | 2.40 | 1.9 |

TABLE 8.1

Particle size distribution using a Coulter LS 100 with microvolume module after ultrasonic treatment (X % of the particles are larger than Y μm)

| Example no. | Mean value μm | Median value μm | Maximum μm | X = 5% Y μm | X = 10% Y μm | X = 50% Y μm | X = 90% Y μm | X = 95% Y μm | Bead size distribution by screen analysis | | | |
|---|---|---|---|---|---|---|---|---|---|---|---|---|
| | | | | | | | | | >300 μm | 150–300 μm | 75–150 μm | <75 μm |
| Ultrasil 7005 | 347.7 | 338.8 | 361.8 | 624.8 | 551.8 | 338.8 | 169.3 | 81.80 | 73.5 | 23.7 | 2.6 | 0.1 |
| 11 | 284.3 | 289.1 | 361.8 | 518.0 | 477.9 | 289.1 | 83.1 | 26.2 | 64.8 | 34.8 | 0.4 | 0 |
| 12 | 145.5 | 116.3 | 153.4 | 403.5 | 324.4 | 116.3 | 15.96 | 10.04 | 55.4 | 44 | 0.5 | 0.2 |
| 13 | 284.9 | 287.3 | 291.9 | 485.7 | 434.9 | 287.3 | 130.2 | 54.1 | 61.6 | 37.9 | 0.4 | 0.1 |
| 15 | 251.4 | 240.4 | 291.9 | 515.9 | 444.6 | 240.4 | 73.45 | 20.64 | 61.4 | 37.9 | 0.4 | 0.1 |

TABLE 9

| Example no. | Average ethanol content μmol/g | Sears numbers | BET surface area m²/g | Micro pore, (d < 2 nm) ml/g | Mesopore volume, (d = 2–30 nm) ml/g | Mesopore volume, (d = 2–50 nm) ml/g | Pore maximum, mesopores nm | Macropores, volume, (d > 30 nm) ml/g | Macropores, volume, (d > 50 nm) ml/g | Pore maximum, macropores μm | Water content in wt. % | Carbon content in wt. % | Sulfur content (average) in wt. % |
|---|---|---|---|---|---|---|---|---|---|---|---|---|---|
| Ultrasil 7005 | 0 | 23.9 | 185 ± 3 | 0.02 ± 0.01 | 0.41 ± 0.03 | 0.87 ± 0.06 | 19 ± 4 | 3.26 ± 0.2 | 2.91 ± 0.2 | 130 ± 10 | 6.7 | 0.06 | 0.2 |
| 16 | 609 | 21.6 | 142 ± 3 | 0.01 ± 0.01 | 0.33 ± 0.02 | 0.64 ± 0.03 | 22 ± 4 | 3.25 ± 0.2 | 2.80 ± 0.2 | 95 ± 10 | 3.79 | 2.72 | 1.9 |
| 17 | 540 | 21.5 | 145 ± 3 | 0.01 ± 0.01 | 0.35 ± 0.02 | 0.70 ± 0.06 | 24 ± 4 | 3.34 ± 0.2 | 2.88 ± 0.2 | 100 ± 10 | 4.15 | 2.64 | 1.85 |
| 18 | 444 | 21.9 | 150 ± 3 | 0.01 ± 0.01 | 0.37 ± 0.02 | 0.70 ± 0.06 | 25 ± 4 | 3.49 ± 0.2 | 3.02 ± 0.2 | 140 ± 10 | 5.07 | 2.17 | 1.8 |

TABLE 10

| Example no. | Average ethanol content μmol/g | Sears numbers | BET surface area m²/g | Micro pores, (d < 2 nm) ml/g | Mesopore volume, (d = 2–30 nm) ml/g | Mesopore volume, (d = 2–50 nm) ml/g | Pore maximum, mesopores nm | Macropores, volume, (d > 30 nm) ml/g | Macropores, volume, (d > 50 nm) ml/g | Pore maximum, macropores μm | Water content in wt. % | Carbon content in wt. % | Sulfur content (average) in wt. % |
|---|---|---|---|---|---|---|---|---|---|---|---|---|---|
| Ultrasil 7005 | 0 | 23.9 | 185 ± 3 | 0.02 ± 0.01 | 0.41 ± 0.03 | 0.87 ± 0.06 | 19 ± 4 | 3.26 ± 0.2 | 2.91 ± 0.2 | 130 ± 10 | 6.7 | 0.06 | 0.2 |
| 19 | 502 | 21.8 | 144 ± 3 | 0.01 ± 0.01 | 0.35 ± 0.02 | 0.72 ± 0.06 | 23 ± 4 | 3.36 ± 0.2 | 2.90 ± 0.2 | 100 ± 10 | 4.09 | 2.45 | 1.85 |
| 20 | 472 | 20.6 | 147 ± 3 | 0.01 ± 0.01 | 0.35 ± 0.02 | 0.69 ± 0.06 | 25 ± 4 | 3.29 ± 0.2 | 2.84 ± 0.2 | 100 ± 10 | 4.28 | 2.40 | 1.9 |
| 21 | 499 | 20.5 | 148 ± 3 | 0.01 ± 0.01 | 0.36 ± 0.02 | 0.68 ± 0.06 | 28 ± 4 | 3.28 ± 0.2 | 2.80 ± 0.2 | 105 ± 10 | 4.95 | 2.30 | 1.9 |

TABLE 10.1

Particle size distribution using a Coulter LS 100 with microvolume module after ultrasonic treatment (X % of the particles are larger than Y μm)

| Example no. | Mean value μm | Median value μm | Maximum μm | X = 5% Y μm | X = 10% Y μm | X = 50% Y μm | X = 90% Y μm | X = 95% Y μm | Bead size distribution by screen analysis | | | |
|---|---|---|---|---|---|---|---|---|---|---|---|---|
| | | | | | | | | | >300 μm | 150–300 μm | 75–150 μm | <75 μm |
| Ultrasil 7005 | 347.7 | 338.8 | 361.8 | 624.8 | 551.8 | 338.8 | 169.3 | 81.80 | 73.5 | 23.7 | 2.6 | 0.1 |
| 16 | 29.24 | 28.53 | 38.08 | 55.84 | 50.53 | 28.53 | 9.58 | 7.07 | 38.6 | 55.8 | 4.2 | 1.6 |
| 17 | 32.44 | 31.80 | 42.39 | 62.27 | 56.09 | 31.80 | 10.08 | 7.39 | 39 | 55.1 | 5 | 0.9 |
| 18 | 28.46 | 27.86 | 38.08 | 53.71 | 48.32 | 27.86 | 9.81 | 7.28 | 38.2 | 54.2 | 4.1 | 3.5 |
| 19 | 31.64 | 31.07 | 42.39 | 60.37 | 54.26 | 31.07 | 10.18 | 7.49 | 46.7 | 48.7 | 3.8 | 0.8 |
| 20 | 28.58 | 28.04 | 38.08 | 53.84 | 48.49 | 28.04 | 9.81 | 7.28 | 45 | 50.2 | 2.8 | 2 |
| 21 | 28.49 | 27.85 | 38.08 | 54.01 | 48.58 | 27.85 | 9.73 | 7.23 | 40.3 | 52.9 | 4.3 | 2.5 |

TABLE 11

| | Number of particles considered | Stati-stical function | Shape factor | | | | Circle factor | | | |
|---|---|---|---|---|---|---|---|---|---|---|
| | | | Minimum | Maximum | Mean value | Standard deviation | Minimum | Maximum | Mean value | Standard deviation |
| Ultrasil 7005 | 116 | | 0.508 | 0.996 | 0.899 | 0.0974 | 0.147 | 0.982 | 0.653 | 0.192 |
| Example no. 2 | 233 | | 0.625 | 0.991 | 0.900 | 0.0807 | 0.144 | 0.985 | 0.644 | 0.203 |
| Coupsil 8108 powder | 822 | | 0.302 | 1.000 | 0.801 | 0.1470 | 0.121 | 0.999 | 0.534 | 0.195 |

TABLE 12

| ID class | from | to | ID class | from | to |
|---|---|---|---|---|---|
| 1 | 0.00 | 0.05 | 11 | 0.50 | 0.55 |
| 2 | 0.05 | 0.1 | 12 | 0.55 | 0.6 |
| 3 | 0.10 | 0.15 | 13 | 0.60 | 0.65 |
| 4 | 0.15 | 0.2 | 14 | 0.65 | 0.7 |
| 5 | 0.20 | 0.25 | 15 | 0.70 | 0.75 |
| 6 | 0.25 | 0.3 | 16 | 0.75 | 0.8 |
| 7 | 0.30 | 0.35 | 17 | 0.80 | 0.85 |
| 8 | 0.35 | 0.4 | 18 | 0.85 | 0.9 |
| 9 | 0.40 | 0.45 | 19 | 0.90 | 0.95 |
| 10 | 0.45 | 0.5 | 20 | 0.95 | 1 |

A micrograph measuring 178 μm×126 μm is taken of the sample Coupsil 8108 (powder) (Table 11) at a magnification of 500:1 using the scanning electron microscope and the image obtained is selected statistically on the basis of the criteria set out in Table 12 and analyzed statistically with regard to shape factor and circle factor.

The ID classes (Table 12) select and define the discrete criteria for shape factor and circle factor from the statistical analyses.

The particle size distributions by laser diffraction without ultrasonic treatment are set out in Table 13.

TABLE 13

Particle size determination using a Coulter LS 100 and dry powder module
(X % of the particles are larger than Y μm)

| | Mean value μm | Median value μm | Maximum μm | X = 5% Y μm | X = 10% Y μm | X = 50% Y μm | X = 90% Y μm | X = 95% Y μm | Bead size distribution by screen analysis | | | |
|---|---|---|---|---|---|---|---|---|---|---|---|---|
| | | | | | | | | | >300 μm | >150 μm, <300 μm | >75 μm; <150 μm | <75 μm |
| Example no. | | | | | | | | | | | | |
| Ultrasil 7005 | 347.2 | 332.0 | 325.0 | 546.9 | 493.7 | 332.0 | 226.1 | 205.0 | | | | |
| 2 | 330.2 | 321.0 | 325.0 | 528.5 | 477.5 | 321.0 | 207.2 | 174.2 | 75.1 | 20.7 | 4 | 0.2 |
| 4 | 352.7 | 337.9 | 325.0 | 557.8 | 504.3 | 337.9 | 225.5 | 203.4 | 71.5 | 25.4 | 3 | 0.2 |
| 5 | 360.3 | 346.2 | 361.8 | 565.6 | 512.1 | 346.2 | 231.2 | 207.7 | 51.3 | 46.7 | 1.5 | 0.5 |
| 11 | 356.6 | 341.1 | 325.0 | 563.7 | 509.4 | 341.1 | 229.3 | 207.2 | 64.8 | 34.8 | 0.4 | 0 |
| 17 | 302.6 | 293.7 | 291.9 | 504.9 | 452.3 | 293.7 | 180.3 | 136.6 | 39 | 55.1 | 5 | 0.9 |
| 20 | 342.3 | 333.0 | 325.0 | 560.5 | 506.0 | 333.0 | 208.0 | 172.4 | 45 | 52.9 | 4.3 | 2.5 |
| Example according to | | | | | | | | | | | | |
| DE10122269.6 | 25.5 | 17.7 | 30.7 | 74.3 | 57.2 | 17.7 | 2.5 | 1.7 | 5.2 | 8.6 | 57.3 | 28.9 |
| Coupsil 8108 powder | 25.9 | 18.5 | 34.2 | 76.3 | 60.8 | 18.5 | 2.4 | 1.6 | 3.9 | 7.6 | 52.3 | 36.2 |
| Coupsil 8108 granules | 483.9 | 504.9 | 853.0 | 865.7 | 831.5 | 504.9 | 45.8 | 10.8 | 89.3 | 3.2 | 4.3 | 3.1 |

Tables 6–10 show the analytical results.

Micrographs measuring 5.65×4 mm are taken of the samples Ultrasil 7005 and Example no. 2 (Table 11) at a magnification of 20:1 (Ultrasil 7005:2 micrographs; sample no. 2:4 micrographs) using the scanning electron microscope and the images obtained are selected statistically on the basis of the criteria set out in Table 12 and analyzed statistically with regard to shape factor and circle factor.

Examples for the Use of Fillers According to the Invention in Rubber Compounds

Production of Rubber Compounds

The formulation used for the rubber compounds is shown in Table 14 below. The unit phr denotes contents by weight, relative to 100 parts of the crude rubber used. The general method for producing rubber compounds and vulcanizates thereof is described in the following book: "Rubber Technology Handbook", W. Hofmann, Hanser Verlag 1994.

TABLE 14

| Substance | Formulation A in-situ reference [phr] | Formulation B [phr] | Formulation C in-situ reference [phr] | Formulation D reference [phr] |
|---|---|---|---|---|
| Stage 1 | | | | |
| Buna VSL 5025-1 | 96 | 96 | 96 | 96 |
| Buna CB 24 | 30 | 30 | 30 | 30 |
| Ultrasil 7005 | 80 | — | — | — |
| Ultrasil VN 3 GR | | | 80 | |
| Silane-modified silica according to the invention | — | 83 | — | — |
| VP Coupsil 8108 | — | — | — | 83 |
| ZnO | 3 | 3 | 3 | 3 |
| Stearic acid | 2 | 2 | 2 | 2 |
| Naftolen ZD | 10 | 10 | 10 | 10 |
| Vulkanox 4020 | 1.5 | 1.5 | 1.5 | 1.5 |
| Protector G35P | 1 | 1 | 1 | 1 |
| Si 69 | 6.4 | — | 6.4 | — |
| Stage 2 | | | | |
| Batch from stage 1 | | | | |
| Stage 3 | | | | |
| Batch from stage 2 | | | | |
| Vulkacit D | 2 | 2 | 2 | 2 |
| Vulkacit CZ | 1.5 | 1.5 | 1.5 | 1.5 |
| Sulfur | 1.5 | 1.5 | 1.5 | 1.5 |

The polymer VSL 5025-1 is a solution-polymerized SBR copolymer from Bayer AG with a styrene content of 25 wt. % and a butadiene content of 75 wt. %. 73% of the butadiene is 1,2-linked, 10% cis-1,4-linked and 17% trans-1,4-linked. The copolymer contains 37.5 phr of oil and displays a Mooney viscosity (ML 1+4/100° C.) of 50±4.

The polymer Buna CB 24 is a cis-1,4-polybutadiene (neodymium-type) from Bayer AG with a cis-1,4 content of 97%, a trans-1,4 content of 2%, a 1,2 content of 1% and a Mooney viscosity of 44±5.

Naftolen ZD from Chemetall is used as the aromatic oil. Vulkanox 4020 is a 6PPD from Bayer AG and Protector G35P is an anti-ozonant wax from HB-Fuller GmbH. Vulkacit D (DPG) and Vulkacit CZ (CBS) are commercial products from Bayer AG.

The coupling reagent Si 69 is a bis-(triethoxysilyl propyl) tetrasulfide from Degussa AG. Ultrasil 7005 is a beaded, readily dispersible precipitated silica from Degussa AG with a BET surface area of 185 m²/g. Ultrasil VN 3 is also a precipitated silica from Degussa AG with a BET surface area of 175 m²/g. VP Coupsil 8108 is a known silane-modified filler and is available from Degussa AG as an experimental product. It is the silica Ultrasil VN 3, presilanized with 8 parts by weight of Si 69 per 100 parts by weight of Ultrasil VN 3.

The rubber compounds are produced in an internal mixer according to the mixing instructions in Table 15.

TABLE 15

| Stage 1 | |
|---|---|
| Settings | |
| Mixing unit | Werner & Pfleiderer E-type |
| Speed | 70 rpm |
| Ram force | 5.5 bar |
| Empty volume | 1.58 l |
| Fill ratio | 0.56 |
| Throughput temp. | 70° C. |
| Mixing process | |
| 0 to 1 min | Buna VSL 5025-1 + Buna CB 24 |
| 1 to 3 min | ½ silica or presilanized silica, ZnO, stearic acid, Naftolen ZD, optionally silane |
| 3 to 4 min | ½ silica or presilanized silica, antioxidant |
| 4 min | Clean |
| 4 to 5 min | Mix |
| 5 min | Clean |
| 5 to 6 min | Mix and remove |
| Batch temp. | 140–155° C. |
| Storage | 24 h at room temperature |
| Stage 2 | |
| Settings | |
| Mixing unit | As for stage 1, apart from |
| Throughput temp. | 80° C. |
| Fill ratio | 0.53 |
| Mixing process | |
| 0 to 2 min | Break up batch from stage 1 |
| 2 to 5 min | Maintain batch temperature at 155° C. by varying the speed |
| 5 min | Remove |
| Batch temp. | 155° C. |
| Storage | 4 h at room temperature |
| Stage 3 | |
| Settings | |
| Mixing unit | As for stage 1 except for |
| Speed | 40 rpm |
| Fill ratio | 0.50 |
| Throughput temp. | 50° C. |
| Mixing process | |
| 0 to 2 min | Batch from stage 2, accelerator, sulfur |
| 2 min | Remove and sheet out on laboratory mixing rolls (diameter 200 mm, length 450 mm, throughput temperature 50° C.) Homogenize: Score 3x on left, 3x on right and fold over Pass through 8x with narrow nip (1 mm) and 3x with wide nip (3.5 mm) Remove sheet. |
| Batch temp. | 85–95° C. |

The rubber test methods are summarised in Table 16.

TABLE 16

| Physical test | Standard/conditions |
|---|---|
| ML 1 + 4, 100° C., stage 3 | DIN 53523/3, ISO 667 |
| Cure-meter test, 165° C. | DIN 53529/3, ISO 6502 |
| Dmax – Dmin [dNm] | |
| t10% and t90% [min] | |
| Tensile test on ring, 23° C. | DIN 53504, ISO 37 |
| Tensile strength [MPa] | |
| Moduli [MPa] | |
| Elongation at break [%] | |
| Shore-A hardness, 23° C. [SH] | DIN 53 505 |
| Viscoelastic properties, | DIN 53 513, ISO 2856 |
| 0 and 60° C., 16 Hz, 50 N initial force and 25 N amplitude force | |
| Dynamic modulus E* [MPa] | |

TABLE 16-continued

| Physical test | Standard/conditions |
|---|---|
| Loss factor tan δ [ ] | |
| Ball rebound, 23° C., 60° C. [%] | ASTM D 5308 |
| DIN abrasion, 10 N force [mm³] | DIN 53 516 |

Compound Examples 1 to 4

In compound examples 1 to 4 the reference mixture mixed in situ (formulation A) with 6.4 phr of the coupling reagent Si 69 is compared with four compounds (formulation B) with the silane-modified silicas according to the invention as reproduced in Table 17.

TABLE 17

| | Compound example: | | | |
|---|---|---|---|---|
| | -1- | -2- | -3- | -4- |
| Example no. according to Tables 1, 2, 3, 4 and 5: | 2 | 11 | 17 | 20 |

Examples for the production of the fillers according to the invention were described in Tables 1, 2, 3, 4 and 5. The formulations used (A) and (B) are set out in Table 14 and the mixing instructions used are shown in Table 15.

The results of the rubber tests are summarised in Tables 18 to 21.

TABLE 18

| | | Compound example | |
|---|---|---|---|
| | | In-situ reference Formulation -1- | |
| | | (A) | (B) |
| ML (1 + 4) | [ME] | 72 | 88 |
| Dmax − Dmin | [dNm] | 18.1 | 20.3 |
| t10% | [min] | 1.2 | 0.9 |
| t90% | [min] | 23.4 | 19.0 |
| Shore-A hardness | [SH] | 66 | 67 |
| Tensile strengtht | [MPa] | 14.5 | 12.9 |
| Modulus 100% | [MPa] | 2.2 | 2.4 |
| Modulus 300% | [MPa] | 10.2 | 11.3 |
| RF 300%/100% | [ ] | 4.6 | 4.7 |
| Elongation at break | [%] | 380 | 330 |
| DIN abrasion | [mm³] | 78 | 77 |
| Ball rebound, 60° C. | [%] | 60 | 59 |
| E* (0° C.) | [MPa] | 24.1 | 35.1 |
| tanδ (0° C.) | [ ] | 0.459 | 0.420 |
| E* (60° C.) | [MPa] | 8.0 | 11.0 |
| tanδ (60° C.) | [ ] | 0.146 | 0.145 |

TABLE 19

| | | Compound example | |
|---|---|---|---|
| | | In-situ reference Formulation -2- | |
| | | (A) | (B) |
| ML (1 + 4) | [ME] | 69 | 85 |
| Dmax − Dmin | [dNm] | 17.3 | 11.0 |
| t10% | [min] | 1.5 | 0.5 |
| t90% | [min] | 20.0 | 23.3 |
| Shore-A hardness | [SH] | 62 | 64 |
| Tensile strength | [MPa] | 12.8 | 14.9 |
| Modulus 100% | [MPa] | 1.8 | 2.0 |
| Modulus 300% | [MPa] | 8.6 | 10.0 |
| RF 300%/100% | [ ] | 4.8 | 5.0 |
| Elongation at break | [%] | 390 | 390 |
| DIN abrasion | [mm³] | 81 | 80 |
| Ball rebound, 60° C. | [%] | 58 | 59 |
| E* (0° C.) | [MPa] | 22.2 | 30.5 |
| tanδ (0° C.) | [ ] | 0.448 | 0.445 |
| E* (60° C.) | [MPa] | 8.1 | 9.8 |
| tanδ (60° C.) | [ ] | 0.135 | 0.136 |

TABLE 20

| | | Compound example | |
|---|---|---|---|
| | | In-situ reference Formulation -3- | |
| | | (A) | (B) |
| ML (1 + 4) | [ME] | 76 | 81 |
| Dmax − Dmin | [dNm] | 15.8 | 16.5 |
| t10% | [min] | 1.6 | 1.2 |
| t90% | [min] | 15.2 | 16.1 |
| Shore-A hardness | [SH] | 63 | 61 |
| Tensile strength | [MPa] | 12.6 | 13.4 |
| Modulus 100% | [MPa] | 2.3 | 2.1 |
| Modulus 300% | [MPa] | 11.5 | 10.7 |
| RF 300%/100% | [ ] | 5.0 | 5.1 |
| Elongation at break | [%] | 320 | 350 |
| DIN abrasion | [mm³] | 62 | 74 |
| Ball rebound, 60° C. | [%] | 63 | 63 |
| E* (0° C.) | [MPa] | 20.9 | 21.5 |
| tanδ (0° C.) | [ ] | 0.454 | 0.452 |
| E* (60° C.) | [MPa] | 8.3 | 8.2 |
| tanδ (60° C.) | [ ] | 0.124 | 0.129 |

TABLE 21

| | | Compound example | |
|---|---|---|---|
| | | In-situ reference Formulation -4- | |
| | | (A) | (B) |
| ML (1 + 4) | [ME] | 76 | 83 |
| Dmax − Dmin | [dNm] | 15.8 | 17.6 |
| t10% | [min] | 1.6 | 1.0 |
| t90% | [min] | 15.2 | 15.5 |
| Shore-A hardness | [SH] | 63 | 62 |
| Tensile strength | [MPa] | 12.6 | 11.5 |
| Modulus 100% | [MPa] | 2.3 | 2.2 |
| Modulus 300% | [MPa] | 11.5 | 11.3 |
| RF 300%/100% | [ ] | 5.0 | 5.1 |
| Elongation at break | [%] | 320 | 300 |
| DIN abrasion | [mm³] | 62 | 66 |
| Ball rebound, 60° C. | [%] | 63 | 62 |
| E* (0° C.) | [MPa] | 20.9 | 26.3 |
| tanδ (0° C.) | [ ] | 0.454 | 0.460 |

TABLE 21-continued

| | | Compound example | |
|---|---|---|---|
| | | In-situ reference Formulation -4- | |
| | | (A) | (B) |
| E* (60° C.) | [MPa] | 8.3 | 9.8 |
| tanδ (60° C.) | [ ] | 0.124 | 0.129 |

As can be seen from the data in Tables 18 to 21, the viscosities ML (1+4) and the vulcanization characteristics of the example compounds are at a similar level to those of the in-situ reference compounds. The static and dynamic rubber data is comparable within the limits of conventional variations in rubber tests. The consistently higher value for the reinforcing factor RF 300%/100% for the example compounds in comparison to the in-situ reference compounds indicates a higher silica-silane bonding. This all clearly shows that the use of the silica according to the invention leads to rubber properties that are comparable with or tend to be better than those of the in-situ reference. This cannot be achieved with silanised fillers corresponding to the prior art.

Compound Example: Prior Art

The compound example for the prior art shows that as compared with the in-situ reference compound (formulation C) the rubber properties deteriorate when the commercial presilanized silica VP Coupsil 8108 (formulation D) is used. Formulations (C) and (D) are based on the formulations shown in Table 14. In a variation of the mixing instructions used in formulations (A) and (B) and set out in Table 14, in this example the second mixing stage is mixed at an initial speed of 80 rpm and a throughput temperature of 80° C. This is only a minor deviation, however. The results are set out in Table 22.

TABLE 22

| | | Compound example | |
|---|---|---|---|
| | | In-situ reference Formulation -5- | |
| | | (C) | (D) |
| ML (1 + 4) | [ME] | 60 | 82 |
| Dmax − Dmin | [dNm] | 18.9 | 22.1 |
| t10% | [min] | 1.6 | 1.1 |
| t90% | [min] | 23.2 | 36.0 |
| Shore-A hardness | [SH] | 62 | 69 |
| Tensile strength | [MPa] | 13.0 | 13.0 |
| Modulus 100% | [MPa] | 1.9 | 2.3 |
| Modulus 300% | [MPa] | 8.9 | 9.1 |
| RF 300%/100% | [ ] | 4.7 | 4.0 |
| Elongation at break | [%] | 380 | 380 |
| DIN abrasion | [mm³] | 91 | 88 |
| Ball rebound, 23° C. | [%] | 32 | 33 |
| E* (0° C.) | [MPa] | 15.4 | 20.5 |
| tanδ (0° C.) | [ ] | 0.486 | 0.502 |
| E* (60° C.) | [MPa] | 6.5 | 7.7 |
| tanδ (60° C.) | [ ] | 0.138 | 0.144 |

The values from Table 22 show that the high level of the in-situ reference compound is not achieved when the known, presilanized silica VP Coupsil 8108 is used. Both the higher Mooney viscosity and the higher Shore-A hardness indicate an unsatisfactorily homogeneous silanization, leading to a higher filler network in compound (D). The reinforcing factor RF 300%/100% for compound (D) also drops significantly as compared with reference (C).

The advantage of using the silicas according to the invention lies in the fact that in contrast to the known in-situ silanization used according to the prior art with liquid silanes, such as e.g. Si 69, there is no need to perform a chemical reaction, requiring an optimum process control, during the mixing process. Furthermore, in the known in-situ silanization considerable amounts of alcohol are disadvantageously liberated, which escape from the compound and thus lead to problems in the exhaust air.

The compound examples clearly show that the use in rubber of the presilanized silicas according to the invention results in properties that are comparable to or better than in-situ silanization according to the prior art, without causing the aforementioned disadvantages such as arise in the known in-situ silanization. By contrast, although the cited problem of ethanol evolution during mixing is avoided with the use of commercial presilanised silicas, such as e.g. VP Coupsil 8108, the high technical standard of the in-situ reference is not achieved.

Further modifications and variations will be apparent to those skilled in the art from the foregoing and are intended to be encompassed by the claims appended hereto.

German priority application 102 18 350.3 of Apr. 25, 2002 is relied on and incorporated herein by reference.

The invention claimed is:

1. Silane-modified oxidic or siliceous particulate filler, having a bead fraction below 75 μm of less than 15 wt. %, determined by screen analysis, and a median particle size of 130 to 500 μm, determined by laser diffraction without ultrasonic treatment.

2. The silane-modified oxidic or siliceous filler according to claim 1, wherein particles have a statistically determined mean circle factor of greater than 0.55.

3. The silane-modified oxidic or siliceous filler according to claim 1, wherein particles have a statistically determined mean shape factor of greater than 0.805.

4. The silane-modified oxidic or siliceous filler according to claim 1, wherein particles have a BET surface area of 0.5 m²/g to 500 m²/g.

5. The silane-modified oxidic or siliceous filler according to claim 1, wherein particles have a content of carbon in pure or chemically bonded form of 0.1 to 25 wt. %.

6. The silane-modified oxidic or siliceous filler according to claim 1, wherein particles have a content of physically and chemically bonded alcohol of 0 to 25 wt. %.

7. The silane-modified oxidic or siliceous filler according to claim 1, wherein the residual content of alcohol deriving from the silane is less than 75 mol % of the initial amount of alcohol in the silane used to make the silane-modified oxidic or siliceous filler.

8. The silane-modified oxidic or siliceous filler according to claim 1, wherein the filler is compatible with rubber and displays a fine particle character and reinforcing effect in a polymer matrix.

9. The silane-modified oxidic or siliceous filler according to claim 8, which is a member reflected from the groups consisting of silicates, zeolites, silicas and metal oxides.

10. The silane-modified oxidic or siliceous filler according to claim 9, wherein the silicate is a member reflected from the group consisting of kaolin, mica, kieselgur, diatomaceous earth, talc, wollastonite, clay, glass beads, glass powder, glass fibers.

11. The silane-modified oxidic or siliceous filler according to claim 9, wherein the metal oxide is a member selected from the group consisting of aluminum oxide, aluminum hydroxide, aluminum trihydrate, zinc oxide, boron oxide, magnesium oxide and transition metal oxide.

12. A process for the production of the silane-modified oxidic or siliceous filler according to claim 1, comprising reacting at least one microbeaded or microgranular, oxidic or siliceous filler with at least one silane in a gas compressed by at least one of pressure and temperature.

13. The process for the production of the silane-modified oxidic or siliceous filler according to claim 12, wherein the silane is at least one organosilicon compound having the formula (I)

$$Z\text{-}A\text{-}S_x\text{-}A\text{-}Z \quad (I)$$

in which formula
x is a number from 1 to 14,
Z equals $SiX^1X^2X^3$ and
$X^1$, $X^2$, $X^3$ can each mutually independently denote
  hydrogen (—H),
  halogen or hydroxy (—OH),
  an alkyl substituent,
  an alkyl acid substituent $(C_xH_{2x+1})$—C(=O)O—,
  an alkenyl acid substituent or
  a substituted alkyl or alkenyl acid substituent,
  a linear or branched, cyclic hydrocarbon chain with 1–8 carbon atoms,
  a cycloalkane radical with 5–12 carbon atoms,
  a benzyl radical or
  a halogen- or alkyl-substituted phenyl radical,
  alkoxy groups with linear or branched hydrocarbon chains having $(C_{1-24})$ atoms,
  alkoxy groups with linear or branched polyether chains having $(C_1-C_{24})$ atoms,
  a cycloalkoxy group having $(C_{5-12})$ atoms,
  a halogen- or alkyl-substituted phenoxy group or
  a benzyloxy group,
A is a branched or unbranched, saturated or unsaturated aliphatic, aromatic or mixed aliphatic/aromatic divalent hydrocarbon chain having $C_1$–$C_{30}$ to combine.

14. The process for the production of the silane-modified oxidic or siliceous filler according to claim 13, wherein the silane having formula (I) is a member selected from the group consisting of:
  $[(EtO)_3Si(CH_2)_3]_2S$, $[(EtO)_3Si(CH_2)_3]_2S_2$, $[(EtO)_3Si(CH_2)_3]_2S_3$, $[(EtO)_3Si(CH_2)_3]_2S_4$,
  $[(EtO)_3Si(CH_2)_3]_2S_5$, $[(EtO)_3Si(CH_2)_3]_2S_6$, $[(EtO)_3Si(CH_2)_3]_2S_7$, $[(EtO)_3Si(CH_2)_3]_2S_8$,
  $[(EtO)_3Si(CH_2)_3]_2S_9$, $[(EtO)_3Si(CH_2)_3]_2S_{10}$, $[(EtO)_3Si(CH_2)_3]_2S_{11}$, $[(EtO)_3Si(CH_2)_3]_2S_{12}$,
  $[(EtO)_3Si(CH_2)_3]_2S_{13}$, $[(EtO)_3Si(CH_2)_3]_2S_{14}$,
  $[(C_yH_{2y+1}O)(R)_2Si(CH_2)_3]S_x[(CH_2)_3Si(R)_3]$,
  $[(C_yH_{2y+1}O)_2(R)Si(CH_2)_3]S_x[(CH_2)_3Si(R)_3]$,
  $[(C_yH_{2y+1}O)_3Si(CH_2)_3]S_x[(CH_2)_3Si(R)_3]$, $[(C_yH_{2y+1}O)(R)_2Si(CH_2)_3]S_x[(CH_2)_3Si(C_yH_{2y+1}O)(R)_2]$,
  $[(C_yH_{2y+1}O)_3Si(CH_2)_3]S_x[(CH_2)_3Si(C_yH_{2y+1}O)(R)_2]$,
  $[(C_yH_{2y+1}O)_2(R)Si(CH_2)_3]S_x[(CH_2)_3Si(C_yH_{2y+1}O)(R)_2]$,
  $[(C_yH_{2y+1}O)(R)_2Si(CH_2)_3]S_x[(CH_2)_3Si(C_yH_{2y+1}O)_2(R)]$,
  $[(C_yH_{2y+1}O)_2(R)Si(CH_2)_3]S_x[(CH_2)_3Si(C_yH_{2y+1}O)_2(R)]$,
  $[(C_yH_{2y+1}O)_3Si(CH_2)_3]S_x[(CH_2)_3Si(C_yH_{2y+1}O)_2(R)]$,
  $[(C_yH_{2y+1}O)(R)_2Si(CH_2)_3]S_x[(CH_2)_3Si(C_yH_{2y+1}O)_3]$,
  $[(C_yH_{2y+1}O)_2(R)Si(CH_2)_3]S_x[(CH_2)_3Si(C_yH_{2y+1}O)_3]$,
  $[(C_yH_{2y+1}O)_3Si(CH_2)_3]S_x[(CH_2)_3Si(C_yH_{2y+1}O)_3]$,
where x=1–14, y=10–24 and R=(MeO) or/and (EtO), and mixtures of the individual silanes.

15. The process for the production of the silane-modified oxidic or siliceous filler according to claim 12, wherein the silane is at least one organosilicon compound having the formula (II)

$$X^1X^2X^3Si\text{-}A\text{-}S\text{—}SiR^1R^2R^3 \quad (II)$$

in which formula
$X^1$, $X^2$, $X^3$ and A mutually independently have the same meaning as in formula (I), $R^1$, $R^2$, $R^3$ are each mutually independent and denote $(C_1\text{–}C_{16})$ alkyl, $(C_1\text{–}C_{16})$ alkoxy, $(C_1\text{–}C_{16})$ haloalkyl, aryl, $(C_7\text{–}C_{16})$ aralkyl, —H, halogen or $X^1X^2X^3Si\text{-}A\text{-}S\text{—}$.

The process for the production of the silane-modified oxidic or siliceous filler according to claim 12, wherein the silane is at least one organosilicon compound having the general formula (III)

$$X^1X^2X^3Si\text{-}Alk \quad (III)$$

in which formula
$X^1$, $X^2$, $X^3$ each mutually independently have the same meaning as in formula (I) and Alk is a straight-chain, branched or cyclic $(C_1\text{–}C_{24})$ alkyl, $(C_1\text{–}C_{24})$ alkoxy, halogen, hydroxy, nitrile, thiol, $(C_1\text{–}C_4)$ haloalkyl, —$NO_2$, $(C_1\text{–}C_8)$ thioalkyl, —$NH_2$, —$NHR^1$, —$NR^1R^2$, alkenyl, allyl, vinyl, aryl or a $(C_7\text{–}C_{16})$ aralkyl substituent.

16. The process for the production of the silane-modified oxidic or siliceous filler according to claim 12, wherein the silane is a member selected from the group consisting of $(MeO)_3$—Si—$(CH_2)_3$—H, $(EtO)_3$—Si—$(CH_2)_3$—H, $(MeO)_3$—Si—$C(CH_3)_3$, $(EtO)_3$—Si—$C(CH_3)_3$, $(MeO)_3$—Si—$(CH_2)_8$—H, $(EtO)_3$—Si—$(CH_2)_8$—H, $(MeO)_3$—Si—$(CH_2)_{16}$—H, $(EtO)_3$—Si—$(CH_2)_{16}$—H, $Me_3Si$—OMe, $Me_3Si$—OEt, $Me_3Si$—Cl, $Et_3Si$—Cl, $(MeO)_3Si$—CH=$CH_2$, $(EtO)_3Si$—CH=$CH_2$, $(Me_3Si)_2N$—C(O)—H, $(Me_3Si)_2$N—H and mixtures thereof.

17. The process for the production of the silane-modified oxidic or siliceous filler according to claim 16, wherein the silane is a member selected from the group consisting of $(MeO)_3$—Si—$(CH_2)_3$—H, $(EtO)_3$—Si—$(CH_2)_3$—H, $(MeO)_3$—Si—$C(CH_3)_3$, $(EtO)_3$—Si—$C(CH_3)_3$, $(MeO)_3$—Si—$(CH_2)_8$—H, $(EtO)_3$—Si—$(CH_2)_8$—H, $(MeO)_3$—Si—$(CH_2)_{16}$—H, $(EtO)_3$—Si—$(CH_2)_{16}$—H, $Me_3Si$—OMe, $Me_3Si$—OEt, $Me_3Si$—Cl, $Et_3Si$—Cl, $(MeO)_3Si$—CH=$CH_2$, $(EtO)_3Si$—CH=$CH_2$, $(Me_3Si)_2N$—C(O)—H, $(Me_3Si)_2N$—H and mixtures thereof.

18. The process for the production of the silane-modified oxidic or siliceous filler according to claim 12, wherein the silane is at least one organosilicon compound having the formula (IV) or (V)

$$[[(ROC(=O))_P\text{-}(G)_j]_k\text{-}Y\text{—}S]_r\text{-}G\text{-}(SiX^1X^2X^3)_S \quad (IV)$$

$$[(X^1X^2X^3Si)_q\text{-}G]_a\text{—}[Y\text{—}[S\text{-}G\text{-}SiX^1X^2X^3]_b]_c \quad (V)$$

is used as the silane,
in which formulae Y represents a polyvalent species $(Q)_zD(=E)$, and
p is 0 to 5, r is 1 to 3, z is 0 to 2; q is 0 to 6, a is 0 to 7, b is 1 to 3, j is 0 to 1, but if p=1 it can also commonly be 0, c is 1 to 6, t is 0 to 5, s is 1 to 3, k is 1 to 2, under the proviso that
(1) if (D) is a carbon, sulfur or sulfonyl, a+b=2 and k=1,
(2) if (D) is a phosphorus atom, a+b=3 provided that c≧1 and b=1, whereby a=c+1,
(3) if (D) is a phosphorus atom, k=2,
Y represents a polyvalent species $(Q)_zD(=E)$, in each of these groups the atom (D) is doubly bonded to the heteroatom (E), which in turn is bonded to the sulfur atom (S), which is coupled to the silicon atom (Si) by means of a group (G), $R^1$ mutually independently denotes H, a straight, cyclic or branched alkyl chain, optionally alkyl chains containing unsaturated components or aromatics and displaying the same meanings as in formula (II), G independently of the other substituents denotes hydrogen, a straight, cyclic or branched alkyl chain with ($C_1$–$C_{18}$), whereby the alkyl chains can optionally contain an unsaturated component, if p=0 in the formula, G is preferably hydrogen (H), G does not correspond to the structure of an α,β-unsaturated fragment that is bonded to the Y fragment in such a way that an α,β-unsaturated thiocarbonyl fragment is formed, $X^1$, $X^2$ and $X^3$ each mutually independently have the meaning as in formula (I).

19. The process for the production of the silane-modified oxidic or siliceous filler according to claim 12, wherein the silane is at least one organosilicon compound having the formula (VI)

$X^1X^2X^3$Si-A-Sub     (VI)

where $X^1$, $X^2$, $X^3$ and A, each mutually independently, have the meaning according to formula (I) and Sub is —$NH_2$, —SH, —NH(A-Si$X^1X^2X^3$), —N(A-Si$X^1X^2X^3$)$_2$, O—C(O)—CMe=$CH_2$ or —SCN.

20. The process for the production of the silane-modified oxidic or siliceous filler according to claim 19, wherein the silane is a member selected from the groups consisting of ([(MeO)$_3$Si—(CH$_2$)$_3$—]$_2$NH, [(EtO)$_3$Si—(CH$_2$)$_3$—]$_2$NH, [(C$_3$H$_7$O)$_3$Si—(CH$_2$)$_3$—]$_2$NH, (MeO)$_3$Si—(CH$_2$)$_3$—NH$_2$, (EtO)$_3$Si—(CH$_2$)$_3$—NH$_2$, (C$_3$H$_7$O)$_3$Si—(CH$_2$)$_3$—NH$_2$, (MeO)$_3$Si—(CH$_2$)$_3$—NH—(CH$_2$)$_2$—NH$_2$, (EtO)$_3$Si—(CH$_2$)$_3$—NH—(CH$_2$)$_2$—NH$_2$, (C$_3$H$_7$O)$_3$Si—(CH$_2$)$_3$—NH—(CH$_2$)$_2$—NH$_2$, (MeO)$_3$Si—(CH$_2$)$_3$—SH, (EtO)$_3$Si—(CH$_2$)$_3$—SH, (C$_3$H$_7$O)$_3$Si—(CH$_2$)$_3$—SH, (MeO)$_3$Si—(CH$_2$)$_3$—O—C(O)—CMe=$CH_2$, (EtO)$_3$Si—(CH$_2$)$_3$—O—C(O)—CMe=$CH_2$, C$_3$H$_7$O)$_3$Si—(CH$_2$)$_3$—O—C(O)—CMe=$CH_2$, SCN, (EtO)$_3$Si—(CH$_2$)$_3$—SCN, (C$_3$H$_7$O)$_3$Si—(CH$_2$)$_3$—SCN,
[(C$_y$H$_{2y+1}$O)(EtO)$_2$Si(CH$_2$)$_3$]—NH$_2$, [(C$_y$H$_{2y+1}$O)$_2$(EtO)Si(CH$_2$)$_3$]—NH$_2$,
[(C$_y$H$_{2y+1}$O)(EtO)$_2$Si(CH$_2$)$_3$]—SH, [(C$_y$H$_{2y+1}$O)$_2$(EtO)Si(CH$_2$)$_3$]—SH, [(C$_y$H$_{2y+1}$O)(EtO)$_2$Si(CH$_2$)$_3$]—O—C(O)—CMe=$CH_2$, [(C$_y$H$_{2y+1}$O)$_2$(EtO)Si(CH$_2$)$_3$]—O—C(O)—CMe=$CH_2$, where y=10–24, and mixtures thereof.

21. The process for the production of the silane-modified oxidic or siliceous filler according to claim 12, wherein mixtures of the silanes having formulae I–VI are used as the silane.

22. The process for the production of the silane-modified oxidic or siliceous filler according to claim 12, wherein oligomeric or cooligomeric silanes having formulae I–VI or mixtures thereof or mixtures of silanes having formulae I–VI and oligomers or cooligomers thereof are used as the silane.

23. The process for the production of the silane-modified oxidic or siliceous filler according to claim 12, wherein at least one of a natural and a synthetic filler is used as the microbeaded or microgranular, oxidic or siliceous filler.

24. The process for the production of the silane-modified oxidic or siliceous filler according to claim 12, wherein the microbeaded or microgranular, oxidic or siliceous filler is a microbeaded or microgranular kaolin, kieselgur, mica, diatomaceous earth, clay, talc, wollastonite, silicates inter alia in the form of glass beads, glass powder, glass fibres or glass cloth, zeolites, aluminum oxide, aluminum hydroxide or trihydrate, aluminum silicates, silicates, precipitated silicas with BET surface areas measured with gaseous nitrogen of 1 to 1000 m$^2$/g, zinc oxide, boron oxide, magnesium oxide or transition metal oxides.

25. The process for the production of the silane-modified oxidic or siliceous filler according to claim 12, wherein 10–250 parts by weight of microbeaded or microgranular, oxidic or siliceous filler are reacted with 0.1–50 parts by weight of silane.

26. The process for the production of the silane-modified oxidic or siliceous filler according to claim 12, wherein the compressed gasses carbon dioxide, helium, nitrogen, dinitrogen monoxide, sulfur hexafluoride, gaseous alkanes with 1 to 5 C atoms, gaseous alkenes with 2 to 4 C atoms, gaseous alkynes, gaseous dienes, gaseous fluorocarbons, at least one of chlorinated hydrocarbons and chlorofluorocarbons or substituents thereof or ammonia, and mixtures of these substances, are used as the compressed gas.

27. The process for the production of the silane-modified oxidic or siliceous filler according to claim 12, wherein the silane used is undissolved, partially or wholly dissolved in the compressed gas.

28. The process for the production of the silane-modified oxidic or siliceous filler according to claim 12, whereas the pressure is from 1 to 500 bar.

29. The process for the production of the silane-modified oxidic or siliceous filler according to claim 12, wherein the reaction takes place at a temperature of from 0 to 300° C.

30. The process for the production of the silane-modified oxidic or siliceous filler according to claim 12, further comprising keeping the pressure during the reaction constant at various pressure levels for periods of 5–720 min and during this time immersing or stirring the filter in the compressed gas or the compressed gas is passed through it.

31. The process for the production of the silane-modified oxidic or siliceous filler according to claim 12, wherein the microbeaded or microgranular, oxidic or siliceous filler and the silane are first mixed together or brought into contact and then mixed or brought into contact with the gas in compressed form.

32. The process for the production of the silane-modified oxidic or siliceous filler according to claim 12, wherein the microbeaded or microgranular, oxidic or siliceous filler is first mixed together or brought into contact with the gas in compressed form and then mixed or brought into contact with the silane.

33. The process for the production of the silane-modified oxidic or siliceous filler according to claim 12, wherein the silane is first mixed together or brought into contact with the gas in compressed form and then mixed or brought into contact with the corresponding microbeaded or microgranular, oxidic or siliceous filler.

34. The process for the production of the silane-modified oxidic or siliceous filler according to claim 12, wherein additional additives are added to at least one of the microbeaded or microgranular, oxidic or siliceous filler and silane before the reaction in the compressed gas or mixture of gases.

35. The process for the production of the silane-modified oxidic or siliceous filler according to claim 12, wherein the silane-modified oxidic or siliceous filler is brought into contact with additional additives during the reaction in the compressed gas.

36. The process for the production of the silane-modified oxidic or siliceous filler according to claim 12, further comprising adding additional additives into the incoming or outgoing stream of compressed gas passing through the silane-modified oxidic or siliceous filler during the reaction of the microbeaded or microgranular, oxidic or siliceous filler in the compressed gas.

37. The process for the production of the silane-modified oxidic or siliceous filler according to claim 34 wherein said additive is a member selected from the group consisting of ammonia, sulfur dioxide, water, short-chain or long-chain alcohols, short-chain or long-chain polyethers or short-chain or long-chain amines, emulsifiers or short-chain or long-chain silicone oils.

* * * * *